(12) United States Patent
Skelton et al.

(10) Patent No.: US 8,231,555 B2
(45) Date of Patent: Jul. 31, 2012

(54) THERAPY SYSTEM INCLUDING MULTIPLE POSTURE SENSORS

(75) Inventors: Dennis M. Skelton, Bloomington, MN (US); Jon P. Davis, St. Michael, MN (US); Keith A. Miesel, St. Paul, MN (US); Timothy J. Denison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 528 days.

(21) Appl. No.: 12/433,442

(22) Filed: Apr. 30, 2009

(65) Prior Publication Data

US 2010/0280417 A1   Nov. 4, 2010

(51) Int. Cl.
*A61B 5/103* (2006.01)
*A61B 5/117* (2006.01)
*A61B 1/00* (2006.01)
*G06T 15/00* (2011.01)
*A61M 31/00* (2006.01)

(52) U.S. Cl. .......... 600/595; 33/512; 345/419; 600/587; 600/594; 604/66; 607/62; 607/63

(58) Field of Classification Search .................. 345/419; 600/587, 595, 594; 33/512; 604/66; 607/62, 607/63

See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |
| 5,040,534 A | 8/1991 | Mann et al. | |
| 5,040,536 A | 8/1991 | Riff | |

(Continued)

FOREIGN PATENT DOCUMENTS

DE   19831109   1/2000

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Sean Dougherty
(74) *Attorney, Agent, or Firm* — Shumaker & Sieffert, P.A.

(57) ABSTRACT

Posture-responsive therapy is delivered by the medical system based on posture state input from only one of multiple posture sensors at any given time. An example implantable medical system includes a first posture sensor and a second sensor. A processor controls therapy delivery to the patient based on at least one of a patient posture state or a patient activity level determined based on input from only one of the first or second posture sensors. In some examples, one of multiple posture sensors of an implantable posture-responsive medical system is used to automatically reorient another posture sensor (of the system), which has become disoriented. The disoriented posture sensor may be automatically reoriented for one or more posture states at a time.

22 Claims, 17 Drawing Sheets

U.S. PATENT DOCUMENTS

| | | | |
|---|---|---|---|
| 5,058,584 A | 10/1991 | Bourgeois | |
| 5,125,412 A | 6/1992 | Thornton | |
| 5,154,180 A | 10/1992 | Blanchet et al. | |
| 5,158,078 A | 10/1992 | Bennett et al. | |
| 5,167,229 A | 12/1992 | Peckham et al. | |
| 5,233,984 A | 8/1993 | Thompson | |
| 5,275,159 A | 1/1994 | Griebel | |
| 5,312,446 A | 5/1994 | Holschbach et al. | |
| 5,335,657 A | 8/1994 | Terry, Jr. et al. | |
| 5,337,758 A | 8/1994 | Moore et al. | |
| 5,342,409 A | 8/1994 | Mullett | |
| 5,347,289 A * | 9/1994 | Elhardt | 342/448 |
| 5,354,317 A | 10/1994 | Alt | |
| 5,425,750 A | 6/1995 | Moberg | |
| 5,476,483 A | 12/1995 | Bornzin et al. | |
| 5,487,755 A | 1/1996 | Snell et al. | |
| 5,513,645 A | 5/1996 | Jacobson et al. | |
| 5,514,162 A | 5/1996 | Bornzin et al. | |
| 5,558,640 A | 9/1996 | Pfeiler et al. | |
| 5,562,707 A | 10/1996 | Prochazka et al. | |
| 5,593,431 A | 1/1997 | Sheldon | |
| 5,622,428 A | 4/1997 | Bonnet | |
| 5,628,317 A | 5/1997 | Starkebaum et al. | |
| 5,643,332 A | 7/1997 | Stein | |
| 5,645,053 A | 7/1997 | Remmers et al. | |
| 5,674,258 A | 10/1997 | Henschel et al. | |
| 5,711,316 A | 1/1998 | Elsberry et al. | |
| 5,720,770 A | 2/1998 | Nappholz et al. | |
| 5,732,696 A | 3/1998 | Rapoport et al. | |
| 5,741,310 A | 4/1998 | Wittkampf | |
| 5,782,884 A | 7/1998 | Stotts et al. | |
| 5,814,093 A | 9/1998 | Stein | |
| 5,832,932 A | 11/1998 | Elsberry et al. | |
| 5,833,709 A | 11/1998 | Rise et al. | |
| 5,836,989 A | 11/1998 | Shelton | |
| 5,851,193 A | 12/1998 | Arikka et al. | |
| 5,865,760 A | 2/1999 | Lidman et al. | |
| 5,885,471 A | 3/1999 | Ruben et al. | |
| 5,893,883 A | 4/1999 | Torgerson et al. | |
| 5,895,371 A | 4/1999 | Levitas et al. | |
| 5,904,708 A | 5/1999 | Goedeke | |
| 5,911,738 A | 6/1999 | Sikorski et al. | |
| 5,913,727 A | 6/1999 | Ahdoot | |
| 5,919,149 A | 7/1999 | Allum | |
| 5,938,690 A | 8/1999 | Law et al. | |
| 5,941,906 A | 8/1999 | Barreras, Sr. et al. | |
| 5,944,680 A | 8/1999 | Christopherson et al. | |
| 5,957,957 A | 9/1999 | Sheldon | |
| 6,027,456 A | 2/2000 | Feler et al. | |
| 6,038,475 A | 3/2000 | Sikorski et al. | |
| 6,044,297 A | 3/2000 | Sheldon et al. | |
| 6,045,513 A | 4/2000 | Stone et al. | |
| 6,059,576 A | 5/2000 | Brann | |
| 6,095,991 A | 8/2000 | Krausman et al. | |
| 6,099,479 A | 8/2000 | Christopherson et al. | |
| 6,102,874 A | 8/2000 | Stone et al. | |
| 6,120,467 A | 9/2000 | Schallhorn | |
| 6,128,534 A | 10/2000 | Park et al. | |
| 6,134,459 A | 10/2000 | Roberts et al. | |
| 6,157,857 A | 12/2000 | Dimpfel | |
| 6,165,143 A | 12/2000 | Van Lummel | |
| 6,216,537 B1 | 4/2001 | Henschel et al. | |
| 6,259,948 B1 | 7/2001 | Florio et al. | |
| 6,280,409 B1 | 8/2001 | Stone et al. | |
| 6,296,606 B1 | 10/2001 | Goldberg et al. | |
| 6,308,098 B1 | 10/2001 | Meyer | |
| 6,308,099 B1 | 10/2001 | Fox et al. | |
| 6,315,740 B1 | 11/2001 | Singh | |
| 6,327,501 B1 | 12/2001 | Levine et al. | |
| 6,341,236 B1 | 1/2002 | Osorio et al. | |
| 6,351,672 B1 | 2/2002 | Park et al. | |
| 6,368,284 B1 | 4/2002 | Bardy | |
| 6,381,496 B1 | 4/2002 | Meadows et al. | |
| 6,393,325 B1 | 5/2002 | Mann et al. | |
| 6,438,408 B1 | 8/2002 | Mulligan et al. | |
| 6,440,090 B1 | 8/2002 | Schallhorn | |
| 6,449,508 B1 | 9/2002 | Sheldon et al. | |
| 6,459,934 B1 | 10/2002 | Kadhiresan | |
| 6,466,821 B1 | 10/2002 | Pianca et al. | |
| 6,468,234 B1 | 10/2002 | Van der Loos et al. | |
| 6,507,757 B1 | 1/2003 | Swain et al. | |
| 6,514,218 B2 | 2/2003 | Yamamoto | |
| 6,516,749 B1 | 2/2003 | Salasidis | |
| 6,539,249 B1 | 3/2003 | Kadhiresan et al. | |
| 6,547,755 B1 | 4/2003 | Lippe et al. | |
| 6,572,557 B2 | 6/2003 | Tchou et al. | |
| 6,574,507 B1 | 6/2003 | Bonnet | |
| 6,605,038 B1 | 8/2003 | Teller et al. | |
| 6,609,031 B1 | 8/2003 | Law et al. | |
| 6,611,783 B2 | 8/2003 | Kelly, Jr. et al. | |
| 6,620,151 B2 | 9/2003 | Blischak et al. | |
| 6,625,493 B2 | 9/2003 | Kroll et al. | |
| 6,635,048 B1 | 10/2003 | Ullestad et al. | |
| 6,641,542 B2 | 11/2003 | Cho et al. | |
| 6,658,292 B2 | 12/2003 | Kroll et al. | |
| 6,659,968 B1 | 12/2003 | McClure | |
| 6,662,047 B2 | 12/2003 | Sorensen | |
| 6,665,558 B2 | 12/2003 | Kalgren et al. | |
| 6,668,188 B2 | 12/2003 | Sun et al. | |
| 6,687,538 B1 | 2/2004 | Hrdlicka et al. | |
| 6,731,984 B2 | 5/2004 | Cho et al. | |
| 6,740,075 B2 | 5/2004 | Lebel et al. | |
| 6,748,276 B1 | 6/2004 | Daignault, Jr. et al. | |
| 6,752,766 B2 | 6/2004 | Kowallik et al. | |
| 6,773,404 B2 | 8/2004 | Poezevera et al. | |
| 6,782,315 B2 | 8/2004 | Lu et al. | |
| 6,817,979 B2 | 11/2004 | Nihtilä | |
| 6,820,025 B2 | 11/2004 | Bachmann et al. | |
| 6,829,507 B1 | 12/2004 | Lidman et al. | |
| 6,832,113 B2 | 12/2004 | Belalcazar | |
| 6,834,436 B2 | 12/2004 | Townsend | |
| 6,853,863 B2 | 2/2005 | Carter et al. | |
| 6,878,121 B2 | 4/2005 | Krausman et al. | |
| 6,884,596 B2 | 4/2005 | Civelli et al. | |
| 6,890,306 B2 | 5/2005 | Poezevera | |
| 6,895,341 B2 | 5/2005 | Barrey et al. | |
| 6,922,587 B2 | 7/2005 | Weinberg | |
| 6,923,784 B2 | 8/2005 | Stein | |
| 6,928,324 B2 | 8/2005 | Park et al. | |
| 6,937,899 B2 | 8/2005 | Sheldon et al. | |
| 6,937,900 B1 | 8/2005 | Pianca et al. | |
| 6,945,934 B2 | 9/2005 | Bardy | |
| 6,964,641 B2 | 11/2005 | Cho et al. | |
| 6,975,904 B1 | 12/2005 | Sloman | |
| 6,997,882 B1 | 2/2006 | Parker et al. | |
| 6,999,817 B2 | 2/2006 | Park et al. | |
| 7,016,730 B2 | 3/2006 | Ternes | |
| 7,031,772 B2 | 4/2006 | Condie | |
| 7,043,305 B2 | 5/2006 | KenKnight et al. | |
| 7,054,687 B1 | 5/2006 | Andersen | |
| 7,066,910 B2 | 6/2006 | Bauhahn et al. | |
| 7,082,333 B1 | 7/2006 | Bauhahn | |
| 7,092,759 B2 | 8/2006 | Nehls et al. | |
| 7,095,424 B2 | 8/2006 | Satoh et al. | |
| 7,110,820 B2 | 9/2006 | Tcheng et al. | |
| 7,117,036 B2 | 10/2006 | Florio | |
| 7,123,967 B2 | 10/2006 | Weinberg | |
| 7,130,681 B2 | 10/2006 | Gebhardt et al. | |
| 7,130,689 B1 | 10/2006 | Turcott | |
| 7,141,026 B2 | 11/2006 | Aminian et al. | |
| 7,142,921 B2 | 11/2006 | Mattes et al. | |
| 7,149,579 B1 | 12/2006 | Koh et al. | |
| 7,149,584 B1 | 12/2006 | Koh et al. | |
| 7,151,961 B1 | 12/2006 | Whitehurst et al. | |
| 7,155,279 B2 | 12/2006 | Whitehurst et al. | |
| 7,160,252 B2 | 1/2007 | Cho et al. | |
| 7,162,304 B1 | 1/2007 | Bradley | |
| 7,167,743 B2 | 1/2007 | Heruth et al. | |
| 7,167,751 B1 | 1/2007 | Whitehurst et al. | |
| 7,181,281 B1 | 2/2007 | Kroll | |
| 7,189,204 B2 | 3/2007 | Ni et al. | |
| 7,207,947 B2 | 4/2007 | Koh et al. | |
| 7,210,240 B2 | 5/2007 | Townsend et al. | |
| 7,212,862 B2 | 5/2007 | Park et al | |
| 7,214,197 B2 | 5/2007 | Prass | |
| 7,218,964 B2 | 5/2007 | Hill et al. | |
| 7,218,968 B2 | 5/2007 | Condie et al. | |

| Patent/Publication | Date | Inventor |
|---|---|---|
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0075624 A1* | 4/2005 | Miesel .......................... 604/505 |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245858 A1* | 11/2005 | Miesel et al. .................... 604/65 |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0215118 A1* | 9/2008 | Goetz et al. .................... 607/59 |

| | | | |
|---|---|---|---|
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006, 5 pp., http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems,"ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp., 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http ://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

PCT/US2009/049396, Invitation to Pay Additional Fees dated May 12, 2010, 6 pp.

U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No.12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/433,442, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
Office Action dated Aug. 9, 2011 for U.S. Appl. No. 12/433,588, (12 pgs.).
Responsive Amendment dated Nov. 9, 2011 for U.S. Appl. No. 12/433,588, (10 pgs.).

* cited by examiner

THERAPY SYSTEM INCLUDING MULTIPLE POSTURE SENSORS

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from conditions that range from chronic pain, tremor, Parkinson's disease, and epilepsy, to urinary or fecal incontinence, sexual dysfunction, obesity, spasticity, and gastroparesis. As an example, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each parameter in a set of therapeutic parameters specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates to posture-responsive therapy delivery. In examples described herein, a medical device detects a posture state of a patient and delivers therapy based at least in part on the detected patient posture state. For example, in some cases, the medical device adjusts one or more therapy parameter values or other characteristics of the therapy based on the detected posture state.

Various posture states may be defined and detected by a medical device, at least in part, by different sets of posture reference data. In operation, a posture sensor module associated with the medical device compares posture data from one of multiple posture sensors (also referred to as motion or activity sensors) to the posture reference data to detect the posture occupied by the patient. Some examples according to this disclosure include methods and systems in which posture-responsive therapy is delivered based on posture state input from only one of multiple posture sensors included in the implantable medical system.

In one example, an implantable medical system is disclosed that includes a first posture sensor arranged proximate a subcutaneous therapy delivery site within a patient. A second posture sensor is arranged distal to the therapy delivery site within the patient. A processor controls therapy delivery to the patient based on at least one of a patient posture state or a patient activity level determined based on input from only one of the first or second posture sensors.

In another example, an implantable medical system is disclosed that includes an implantable medical device (IMD) including a processor. A first posture sensor is arranged proximate a subcutaneous therapy delivery site within the patient. A second posture sensor is arranged proximate the IMD. The processor is configured to control therapy delivered to a patient based on at least one of a patient posture state or a patient activity level determined based on input from only one of the first or second posture sensors.

In an additional example, a method is disclosed that includes selectively receiving input from one of a first posture sensor or a second posture sensor that is indicative of a posture state of a patient, and delivering therapy to the patient based on the input. At least one of the first and second posture sensors is implanted within the patient.

In an additional example, a system is disclosed that includes means for selectively receiving input from one of a first posture sensor or a second posture sensor that is indicative of a posture state of a patient, and means for delivering therapy to the patient based on the input. At least one of the first and second posture sensors is implanted within the patient.

In still another example, a computer readable medium is disclosed that includes instructions configured to cause one or more processors to perform a method that includes the steps of selectively receiving input from one of a first posture sensor or a second posture sensor that is indicative of a posture state of a patient, and delivering therapy to the patient based on the input. At least one of the first and second posture sensors is implanted within the patient.

In addition to selectively receiving posture state input from only one of multiple posture sensors, some examples disclosed include methods and systems for automatically reorienting one posture sensor for one or more posture states of a patient based on input from another posture sensor. In one such example of automatic posture sensor reorientation, a method is disclosed that includes detecting the disorientation of a first posture sensor for a first posture state of a patient. Posture data is received from a second posture sensor that indicates which one of a plurality of posture states is the first posture state. The first posture sensor is reoriented for the first posture state.

In another example, an implantable medical system is disclosed that includes a first posture sensor arranged proximate a subcutaneous therapy delivery site within a patient. A second posture sensor is arranged distal to the therapy delivery site within the patient. Control electronics operatively connected to the first and second posture sensors and are configured to detect disorientation of one of the first or second posture sensors for a first posture state of the patient, receive posture data from the other of the first or second posture sensors indicating which one of a plurality of posture states is the first posture state, and reorient the one of the first or second posture sensors for the first posture state.

In another example, an implantable medical system is disclosed that includes means for detecting a change in orientation of a first posture sensor of a therapy system that provides posture responsive therapy to a patient, and means for automatically reorienting the first posture sensor based on posture data from a second posture sensor of the therapy system.

In an additional example, a computer readable storage medium is disclosed that includes instructions configured to cause one or more processors to perform a method that includes detecting disorientation of a first posture sensor for a first posture state of a patient. Posture data is received from a second posture sensor that indicates which one of a plurality of posture states is the first posture state. The first posture sensor is reoriented for the first posture state.

In another example, the disclosure is directed to a computer-readable medium comprising instructions. The instructions cause a programmable processor to perform any of the techniques described herein. The instructions may be encoded in the computer-readable medium. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more aspects of the disclosure are set forth in the accompanying drawings and the description below. Other features, objects, and advantages will be apparent from the description and drawings, and from the claims.

DETAILED DESCRIPTION

Figure 1A:
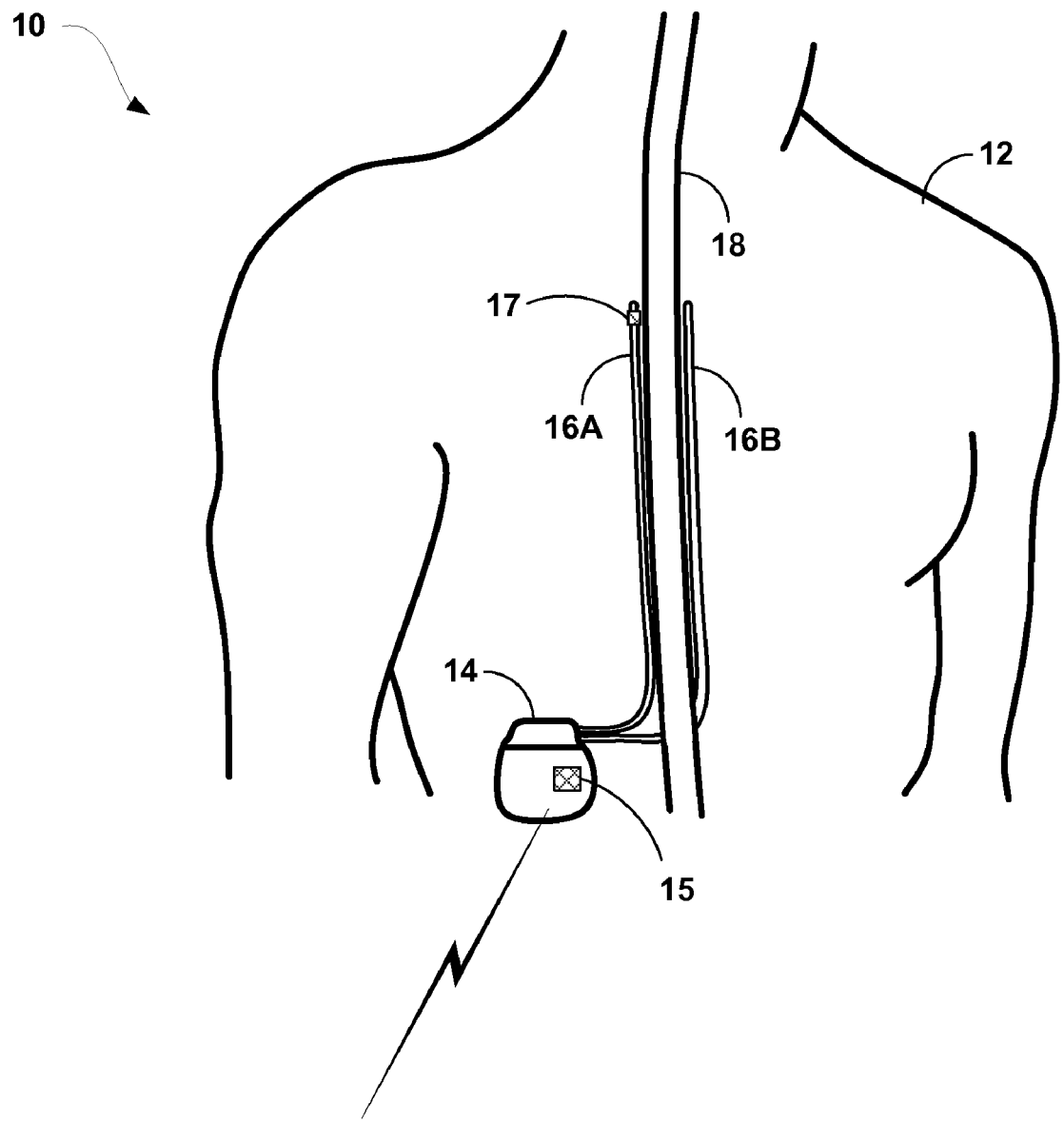
FIG. 1A is a conceptual diagram illustrating an implantable stimulation system including two implantable stimulation leads.

In some medical devices that deliver electrical stimulation therapy or a fluid therapeutic agent, therapeutic efficacy may change as the patient changes posture states. Efficacy refers, in general, to a combination of complete or partial alleviation of symptoms alone, or in combination with a degree of undesirable side effects. In general, a posture state refers to a patient posture or a combination of posture and activity. For example, some posture states, such as upright, may be sub-categorized as upright and active or upright and inactive. Other posture states, such as lying down posture states, may or may not have an activity component, but regardless may have sub-categories such as lying face up or face down, or lying on the right side or on the left side.

Changes in posture state may cause changes in efficacy due to changes in distances between electrodes or other therapy delivery elements, e.g., due to temporary migration of leads or catheters caused by forces or stresses associated with different postures, or from changes in compression of patient tissue against leads or catheters in different posture states. Also, posture state changes may present changes in symptoms or symptom levels, e.g., pain level. For example, for some patients with a chronic lower back condition, sitting may be more painful than lying down. To maintain therapeutic efficacy, it can be desirable to adjust therapy parameters based on different postures and/or activities engaged by the patient to maintain effective therapy. A medical device may adjust therapy by modifying values for one or more therapy parameters, e.g., by specifying adjustments to a specific therapy parameter or by selecting different therapy programs or groups of programs that define different sets of therapy parameter values.

A change in efficacy due to changes in posture state may require the patient to continually manage therapy by manually adjusting certain therapy parameters, such as amplitude, pulse rate, or pulse width in the case of stimulation therapy, or selecting different therapy programs to achieve more efficacious therapy throughout many different posture states. In examples of therapy systems described herein, a medical device employs multiple posture sensors, each of which may generate a signal indicative of the patient posture state. The posture states determined based on the signals from one or more posture sensors may be associated with therapy adjustments made during the sensed posture state to allow a user to review the associations and modify stimulation parameters to better treat the patient. The medical device may also adjust therapy parameters in response to different posture states. Therapy adjustments in response to different posture states may be fully automatic, semi-automatic in the sense that a user may provide approval of proposed changes, user-directed in the sense that the patient may manually adjust therapy based on the posture state indication, or any combination of automation and user interaction.

In accordance with techniques described in this disclosure in which a medical system includes multiple implantable posture sensors, a processor of the medical system controls therapy delivery to the patient based on a patient posture state determined based on input from only one of the multiple posture sensors. Some medical systems include one posture sensor that is arranged proximate a therapy delivery site within the patient and another posture sensor that is arranged proximate the medical device. Other arrangements of the multiple implantable posture sensors of a therapy system are contemplated.

In some examples, the processor in the medical device toggles between activating the first posture sensor and deactivating the second posture sensor, and deactivating the first posture sensor and activating the second posture sensor. In other examples, both posture sensors may be simultaneously active, but the processor may selectively receive input from only one of the sensors. In this way, the processor may toggle between receiving posture state input from one of the first or the second posture sensors. The device may toggle between the first and the second posture sensors based on, e.g., a sensed posture state of the patient. In some cases, the first and the second posture sensors are each associated with one or more of a plurality of patient posture states. In the case of the posture sensors being associated with posture states, the processor toggles to one of the first or second posture sensors based on one or more of the associations between the posture sensor and the sensed posture state of the patient.

In another example, the processor of the medical device may toggle to one of the posture sensors based on a sensed status of the other posture sensor. The status of the posture sensors may include, e.g., sensor failures or malfunctions, becoming disoriented for one or more of the patient posture states, measuring a posture state inaccurately, or sensing a posture state inconsistently with a posture state sensed by the other posture sensor.

The medical device may include an implantable electrical stimulator or fluid delivery device which includes the processor. Examples including the electrical stimulator may also include one or more electrically conductive leads connected to the electrical stimulator. In such cases, one posture sensor may be connected to one of the leads and the other posture sensor may be connected to the electrical stimulator. Similarly, examples including the fluid delivery device may include one or more catheters connected to the fluid delivery device. In such cases, one posture sensor may be connected to one of the catheters and the other posture sensor may be connected to the fluid delivery device.

In addition to selectively receiving posture state input from only one of multiple posture sensors, examples are disclosed in which one posture sensor is automatically reoriented for one or more posture states based on input from another posture sensor. In one such example of automatic posture sensor reorientation, an IMD detects the disorientation of a first posture sensor for a first posture state of a patient. The IMD then receives posture data from a second posture sensor that indicates which one of a plurality of posture states is the first posture state. The first posture sensor is then reoriented by the IMD for the first posture state. In some cases, reorienting the first posture sensor includes receiving posture data from the first posture sensor and defining posture reference data based at least in part on the first posture sensor posture data to define a reoriented posture region that corresponds to the first posture state.

FIG. 1A is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1A, system 10 includes an IMD 14, first posture sensor 15, stimulation leads 16A and 16B, second posture sensor 17 and external programmer 20, all of which are shown in conjunction with patient 12. In the example of FIG. 1A, IMD 14 is an implantable electrical stimulator configured for SCS, e.g., for relief of chronic pain or other symptoms. IMD 14 is implanted within patient 12, and may be, for example, positioned within subcutaneous or submuscular tissue. First posture sensor 15 is physically connected to IMD 14 and is proximate IMD 14. Stimulation leads 16A and 16B are connected to IMD 14 and tunneled through tissue of patient 12 to a therapy delivery site proximate spinal cord 18. Second posture sensor 17 is connected to stimulation lead 16A proximate the therapy delivery site and is closer to the therapy delivery site than first posture sensor 15. Patient 12 is ordinarily a human patient, but may also be a non-human patient including, e.g., a primate, canine, equine, pig, and feline.

IMD 14, in general, has an outer housing that is constructed of a biocompatible material that resists corrosion and degradation from bodily fluids including, e.g., titanium or stainless steel, or a polymeric material including silicone, polyurethane, or other biologically inert polymers. IMD 14 may be implanted within a subcutaneous pocket close to the therapy delivery site. For example, in the example shown in FIG. 1, IMD 14 is implanted within the abdomen of patient 12. However, for SCS, IMD 14 may also be located in the lower back, upper buttocks, or other location to secure IMD 14. In other examples, IMD 14 may be implanted within other suitable sites within patient 12, which may depend, for example, on the target site within patient 12 for the delivery of electrical stimulation therapy.

In still other examples, IMD 14 may be external to patient 12 with percutaneous implantable leads connected between IMD 14 and the target delivery site within patient 12. In examples including an external stimulator, first posture sensor 15 may still be subcutaneously implanted within patient 12 or may be connected to the external stimulator, which may be non-permanently fixed to an external site on patient 12 including, e.g., fixed to the waist of patient 12 with a belt.

Stimulation energy is delivered from IMD 14 to spinal cord 18 of patient 12 via one or more electrodes of implantable leads 16A and 16B (collectively "leads 16"). The electrodes (not shown) may be, e.g., electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In some applications, such as SCS to treat chronic pain, the adjacent implantable leads 16 may have longitudinal axes that are substantially parallel to one another.

The therapy parameters for a therapy program that controls delivery of stimulation therapy by IMD 14 through the electrodes of leads 16 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like in the case IMD 14 is also configured for drug delivery.

In the example of FIG. 1A, leads 16 carry electrodes that are placed adjacent to the target tissue of spinal cord 18. One or more of the electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing. In such cases, second posture sensor 17 may be, e.g., separately implanted within patient 12 distal to IMD 14.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or continuous waveforms. In some examples, the target tissue includes nerves, smooth muscle or skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through spinal cord 18 and to the brain of patient 12. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), peripheral nerve stimulation (PNS), peripheral nerve field stimulation (PNFS), cortical stimulation (CS), pelvic floor stimulation, gastric stimulation, or any other stimulation therapy capable of treating a condition of patient 12. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

As mentioned above, IMD 14 generates and delivers stimulation therapy to a target stimulation site within patient 12 via the electrodes of leads 16 to patient 12 according to one or more therapy programs. A program defines values for one or more parameters that define an aspect of the therapy delivered by IMD 14 according to that program. For example, a program that controls delivery of stimulation by IMD 14 in the form of pulses may define values for voltage or current pulse amplitude, pulse width, and pulse rate for stimulation pulses delivered by IMD 14 according to that program. Moreover, therapy may be delivered according to multiple programs, wherein multiple programs are contained within each of a multiple of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. Stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy. Also, posture state changes may present changes in symptoms or symptom levels including, e.g., pain level.

Therapy system 10 includes a posture state module that determines a patient posture and modifies therapy delivery to patient 12 based on the determined patient posture. In this way, the posture state module helps delivery posture responsive therapy, which helps to minimize interruptions in effective therapy delivery that may ordinarily result from changes in the patient posture state. In the examples described herein, IMD 14 includes the posture state module. However, in other examples, programmer 20 or another device may include the posture state module and control IMD 14 based on a determined posture state.

IMD 14 including the posture state module includes a posture responsive therapy mode in which IMD 14 automatically adjusts stimulation according to the detected posture state to improve therapy efficacy across multiple posture states. For example, the posture state module receives input from multiple posture sensors 15 and 17, which may each be, e.g., an accelerometer that generates a signal with which IMD 14 determines when patient 12 occupies a posture state in which it is appropriate to change the stimulation therapy. Examples of modifications to stimulation therapy that may be made in response to detecting a change in patient posture state include, but are not limited to, changes in stimulation amplitude or electrode combination (e.g., the electrodes selected for therapy delivery and/or the polarity of the selected electrodes). For example, IMD 14 may decrease the stimulation amplitude when the posture state module indicates that patient 12 has lain down. IMD 14 may automatically reduce stimulation amplitude so that patient 12 does not have to do so manually. In addition to "Lying Down," example posture states include "Upright," "Sitting," and so forth. Additionally, one or more of the posture states may have sub-categories including, e.g., "Upright and Active," "Lying Face Down," "Lying Face Up," and so forth.

IMD 14 may be configured to automatically decrease amplitude at a rate suitable to prevent undesirable effects, e.g., such as the effects due to the compression of leads 16 towards spinal cord 18 when patient lies down. In some examples, IMD 14 is configured to decrease the stimulation amplitude to a suitable amplitude value substantially immediately upon detection by IMD 14 that patient 12 is lying down. In other examples, IMD 14 gradually decreases the stimulation amplitude to a suitable amplitude level at a rate of change that is suitable to prevent patient 12 from experiencing undesirable stimulation effects, e.g., due to increased transfer of stimulation energy from, e.g., compression of leads 16 towards spinal cord 18 when patient 12 lies down. In either example, IMD 14 automatically reduces stimulation amplitude upon determining patient 12 has transitioned to a lying down posture state so that patient 12 does not need to manually reduce the stimulation amplitude.

In response to a posture state indication by the posture state module, IMD 14 modifies therapy, e.g., by changing therapy program groups, therapy programs, modifying a stimulation amplitude, pulse width, pulse rate, and/or one or more other parameters, to maintain therapeutic efficacy, as in the above described example of the patient lying down. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

By modifying therapy delivery to patient 12 based on a patient posture state determined by input from one of posture sensors 15, 17, IMD 14 is able to adapt therapy delivery to accommodate varying conditions patient 12 encounters in a variety of posture states during use of therapy system 10. IMD 14 controls therapy delivery to patient 12 based on a patient posture that is determined based on input from only one of first posture sensor 15 or second posture sensor 17 at any given time. In some examples, IMD 14 may toggle between activating first posture sensor 15 connected to IMD 14 and deactivating second posture sensor 17 connected to electrical stimulation lead 16A, and deactivating first posture sensor 15 and activating second posture sensor 17. In other examples, posture sensors 15, 17 may be simultaneously active, but IMD 14 may selectively receive input from only one of the sensors. In this way, the processor may toggle between receiving posture state input from, as opposed to activating one of first or second posture sensors 15, 17. Several conditions may occur during delivery of therapy to patient 12 that affect or dictate which one of first posture sensor 15 or second posture sensor 17 is selected by IMD 14, either for receiving input or for activating. In some examples, IMD 14 toggles to determining a patient posture state based on the signal from one of first or second posture sensors 15, 17 based on the sensed posture state of patient 12, as described in further detail below with referenced to FIGS. 11 and 12. In addition to or instead of toggling to one of sensors 15, 17 based on the sensed posture state of patient 12, IMD 14 may toggle to one of first or second posture sensors 15, 17 based on a sensed status of the other sensor, as described in further detail below with referenced to FIGS. 11 and 12.

The location of first and second posture sensors 15, 17 within patient 12 may make one of the posture sensors 15, 17 more or less effective for sensing different posture states of patient 12. For example, if IMD 14 is implanted in the upper buttocks of patient 12, IMD 14 may be subject to more movement when patient 12 is sitting compared to when patient 12 is standing. In such a case, a processor of IMD 14 may inaccurately or incorrectly determine the patient posture state based on the signal from first posture sensor 15, which is connected to IMD 14, due to the migration of IMD 14 within patient 12 while sitting. Therefore, in some examples described herein, IMD 14 associates one or both of first and second posture sensors 15, 17 with particular posture states for which the respective sensor 15, 17 may more accurately determine the posture state. For example, a processor of IMD 14 may associate second posture sensor 17 with a sitting posture state in a memory of IMD 14. Upon detecting a particular posture state with either posture sensor 15, 17, IMD 14 may toggle to the sensor 15, 17 associated with the posture state in order to verify or confirm that patient 12 is engaged in the posture.

In some examples, posture sensors 15, 17 may be associated with posture states by user programming. For example, patient 12 may progressively assume different posture states and observe whether each of posture sensors 15, 17 is detecting the posture states correctly by, e.g., viewing an user interface that indicates the posture detected by each sensor. Patient 12 or a clinician may then use, e.g. external programmer 20 to instruct IMD 14 to associate one of posture sensors 15, 17 with each of the posture states assumed by the patient. In other examples, IMD 14 may automatically associate posture sensors 15, 17 with different posture states. For example, IMD 14 may compare the posture state detected by each of sensors 15, 17 to one another and to therapy efficacy information received from the patient to surmise which of the two sensors is correctly detecting the posture state of the patient. In any event, after associating posture sensors with particular posture states, IMD 14 may toggle to one of first or second posture sensors 15, 17 based on the sensed posture state of patient 12.

Additionally, in some examples, IMD 14 toggles to one of first or second posture sensors 15, 17 based a sensed status of the other sensor. IMD 14 monitors the status of both of first and second posture sensors 15, 17 for, e.g., malfunctions, failures, inaccurate or incomplete data, or the like. In one example, IMD 14 monitors first and second posture sensors 15, 17 and determines a patient posture state based on the input from only one of the sensors 15, 17 in the event the other fails. In this way, first and second posture sensors 15, 17 provide a redundant posture sensing system with a primary and a backup sensor. In other examples, IMD 14 monitors first and second posture sensors 15, 17 and determines a patient posture state based on the input from only one of the sensors 15, 17 in the event the other sensor becomes disoriented. In still another example, IMD 14 monitors first and second posture sensors 15, 17 and determines a patient posture state based on the input from only one of the sensors 15, 17 in the event the other sensor inaccurately measures a posture state of patient 12. Inaccurate posture state measurements may be detected by comparing data received from first and second posture sensors 15, 17 to one another and may be caused by a particular posture state causing one of the sensor to move within patient 12 and/or one of the sensors losing a posture state orientation.

As described in greater detail with reference to FIGS. 13A, 13B and 14, in some examples, IMD 14 uses one of first or second posture sensors 15, 17 to automatically reorient the other of first or second posture sensors 15, 17 for one or more posture states of patient 12. In some instances a posture sensor, such as sensors 15, 17, may become disoriented relative to the body of patient 12. Disorientation of one of first or second posture sensors 15, 17 may occur in situations in which the physical location of the posture sensor changes with respect to patient 12. As explained above, the location of first and second posture sensors 15, 17 within patient 12 may make them more or less effective for sensing different posture states of patient 12. IMD 14 may, e.g., be implanted in the upper buttocks of patient 12 making the device subject to movement when patient 12 is, e.g., sitting. In such a case, first posture sensor 15 may become disoriented for the posture state of patient 12 due to the migration of IMD 14, and thereby posture sensor 15 within patient 12 over time. For some magnitudes of posture sensor movement within patient 12, reference data used by the processor of IMD 14 to define and detect posture states effectively changes in orientation and, therefore, may no longer be accurate for the posture sensor to detect the posture state of patient 12.

Because IMD 14 may adjust stimulation therapy based on the posture state detected using one of first or second posture sensors 15, 17, IMD 14 may inadvertently deliver the incorrect therapy when patient 12 is in a particular posture state if one of posture sensors 15, 17 becomes disoriented within patient 12. For example, IMD 14 may detect a first posture state of patient 12 when patient 12 is actually in a second posture state. IMD 14 may then adjust therapy delivery to patient 12 to provide efficacious therapy for the first posture state, which may not provide efficacious therapy to patient 12 for the second posture state. In this way, when patient 12 receives the stimulation therapy intended for the first posture state when patient 12 actually occupies the second posture state, patient 12 may not receive efficacious therapy delivery. This example illustrates how the disorientation of one of posture sensors 15, 17 may undermine the efficacy of therapy system 10 by resulting in the delivery of undesirable therapy that is not suited for the actual posture state of patient 12.

One advantage of a therapy system that includes multiple posture sensors that are selectively used to detect posture state is that each of the sensors may be more accurate in determining particular patient postures because of their different locations within patient 12. In some cases, depending on the patient posture state or activity level, first posture sensor 15, which is connected to IMD 14, may be more likely to move within patient 12 than second posture sensor 17 connected to lead 16A near spinal cord 18 of patient 12. It should be noted that although for purposes of illustration reference is made to first posture sensor 15 moving within patient 12, while second posture sensor 17 remains in a more stable position, in other examples, second posture sensor 17 may be more likely to move within patient 12 than first posture sensor 15.

IMD 14 may automatically reorient one of posture sensors 15, 17 based on the other posture sensor. For example, in examples in which second posture sensor 17 is less likely to move within patient 12 than first posture sensor 15, sensor 17 may be used to automatically reorient first posture sensor 15. In some examples, IMD 14 detects the disorientation of first posture sensor 15 for a first posture state of patient 12 by comparing the posture state determination based on the output of posture sensor 15 to the posture state determination based on the output of posture sensor 17. If the posture state determinations do not substantially match, IMD 14 may use second posture sensor 17 to determine the posture state patient 12 actually occupies because posture sensor 17 is less likely to have moved than posture sensor 15. IMD 14 may then reorient first posture sensor 15 for the first posture state without any interaction from patient 12 or a clinician. An example technique for reorienting one posture sensor 15 or 17 based on the other posture sensor is described with respect to FIG. 14.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a clinician (or physician) programmer if it is primarily intended for use by a clinician. In other cases, external programmer 20 may be characterized as a patient programmer if it is primarily intended for use by a patient. A patient programmer is generally accessible to patient 12 and, in many cases, is a portable device that may accompany the patient throughout the patient's daily routine. In general, a clinician programmer may support selection and generation of programs by a clinician for use by IMD 14, whereas a patient programmer may support adjustment and selection of such programs by a patient during ordinary use.

External programmer 20 may present posture state data stored in IMD 14 from the detected posture states of patient 12. The posture state data may be acquired by external programmer 20 to generate posture state information, e.g., therapy adjustment information. IMD 14 may also store any associations between the therapy adjustments input by patient 12 and the posture states for which the therapy adjustments were intended during, e.g., a record mode, i.e., therapy adjustment information. By recording all therapy adjustments made for a program in each of the posture states, external programmer 20 may present therapy adjustment information to the user that indicates stimulation parameters desired by patient 12. For example, the user may identify the most recent stimulation parameters desired by patient 12, the minimum and maximum allowable amplitudes, or even the quantified number of therapy adjustments to indicate that patient 12 is either satisfied with a program or cannot find suitable parameters for a program with many therapy adjustments.

In addition to posture state data, external programmer 20 may present selection options for selecting one of first or second posture sensors 15, 17 to a user. In this way, a user may manually instruct IMD 14 through external programmer 20 to select one of the two posture sensors 15, 17 for determining a posture state of patient 12, instead of automatic selection by IMD 14. In one example, a clinician, e.g. in the process of programming therapy system 10 for patient 12, manually instructs IMD 14 to select one of first posture sensor 15 or second posture sensor 17 for use by IMD 14 for automatically determining a patient posture state based on which of the two will most effectively sense the particular posture state patient 12 is in at the time due to, e.g. the location of the sensor within patient 12.

In another example, patient 12 manually instructs IMD 14 to toggle from one of first or second posture sensors 15, 17 to the other because the current posture sensor appears to be sensing the posture state of patient 12 incorrectly and appears to be malfunctioning or have become disoriented. For example, if patient 12 is upright, but IMD 14 is delivering therapy for a lying down posture state, patient 12 may determine that the currently selected posture sensor 15 or 17 is incorrectly identifying the posture state of patient 12 as lying down. Programmer 20 may transmit an indication to patient 12 that indicates the posture state currently determined by IMD 14 (e.g., via a visible, audible or somatosensory indication). As another example, patient 12 may determine that the current posture sensor is inaccurately determining the patient posture state because therapy delivered by IMD 14 is inefficacious.

Figure 1B:
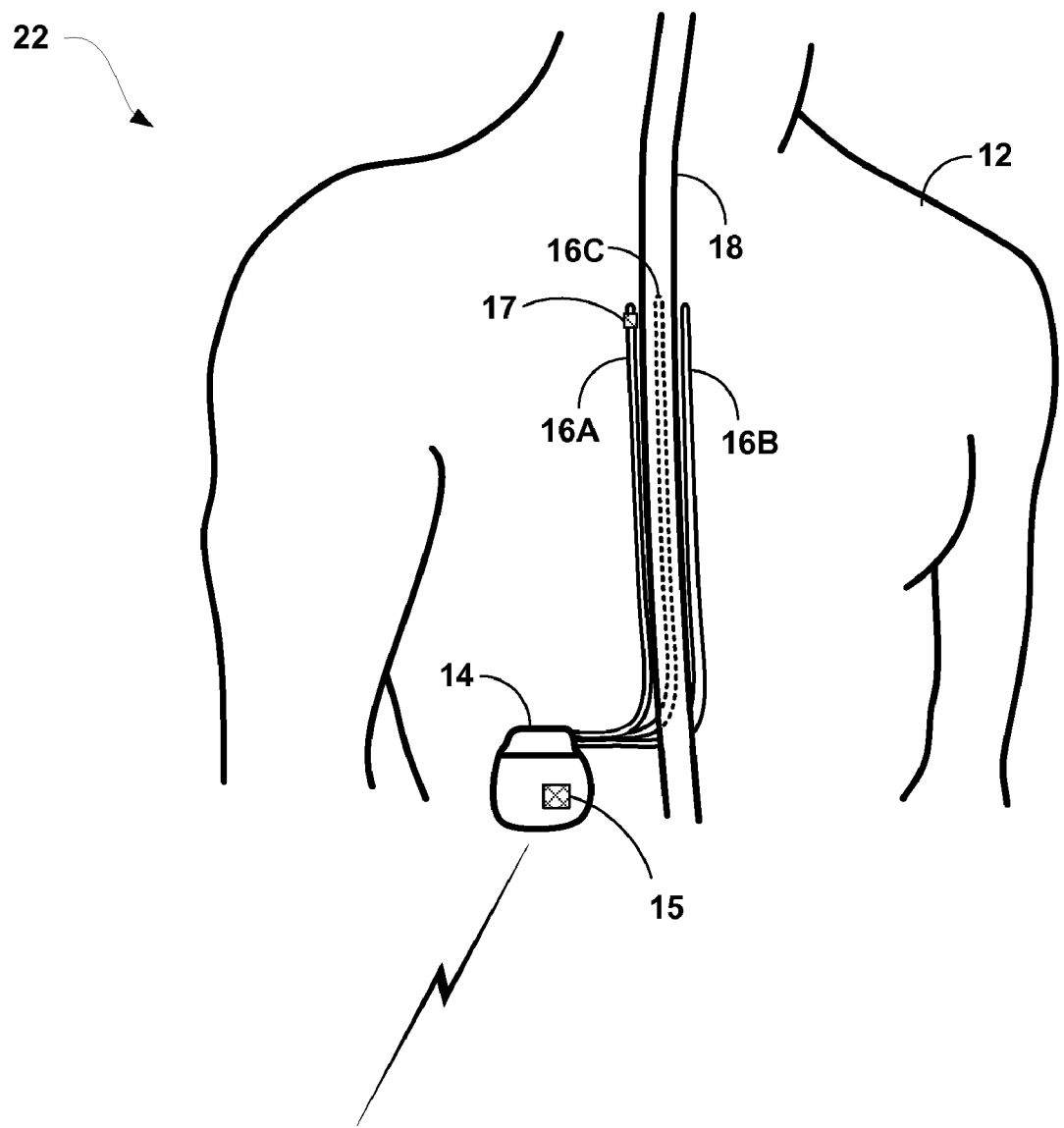
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. In some examples, the third lead 16C includes a greater number of electrodes than leads 16A and 16B and be positioned between leads 16A and 16B or on one side of either lead 16A or 16B.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are also possible. In some cases, electrodes on lead 16C may be smaller in size and/or closer together than the electrodes of leads 16A or 16B. External programmer 20 may be initially told the number and configuration of leads 16 in order to appropriately program stimulation therapy.

Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22. Additionally, IMD 14 may employ only one of first posture sensor 15 or second posture sensor 17 at any given time to automatically or with the aid of user interaction accommodate a variety of conditions encountered during delivery of therapy to patient 12.

Although FIGS. 1A and 1B illustrate therapy systems in which posture sensor 17 is carried by lead 16A, in other examples, posture sensor 17 may be carried by another lead 16B or 16C of the therapy system, or may be physically separate from leads 16A, 16B, and 16C that include one or more stimulation electrodes.

Figure 1C:
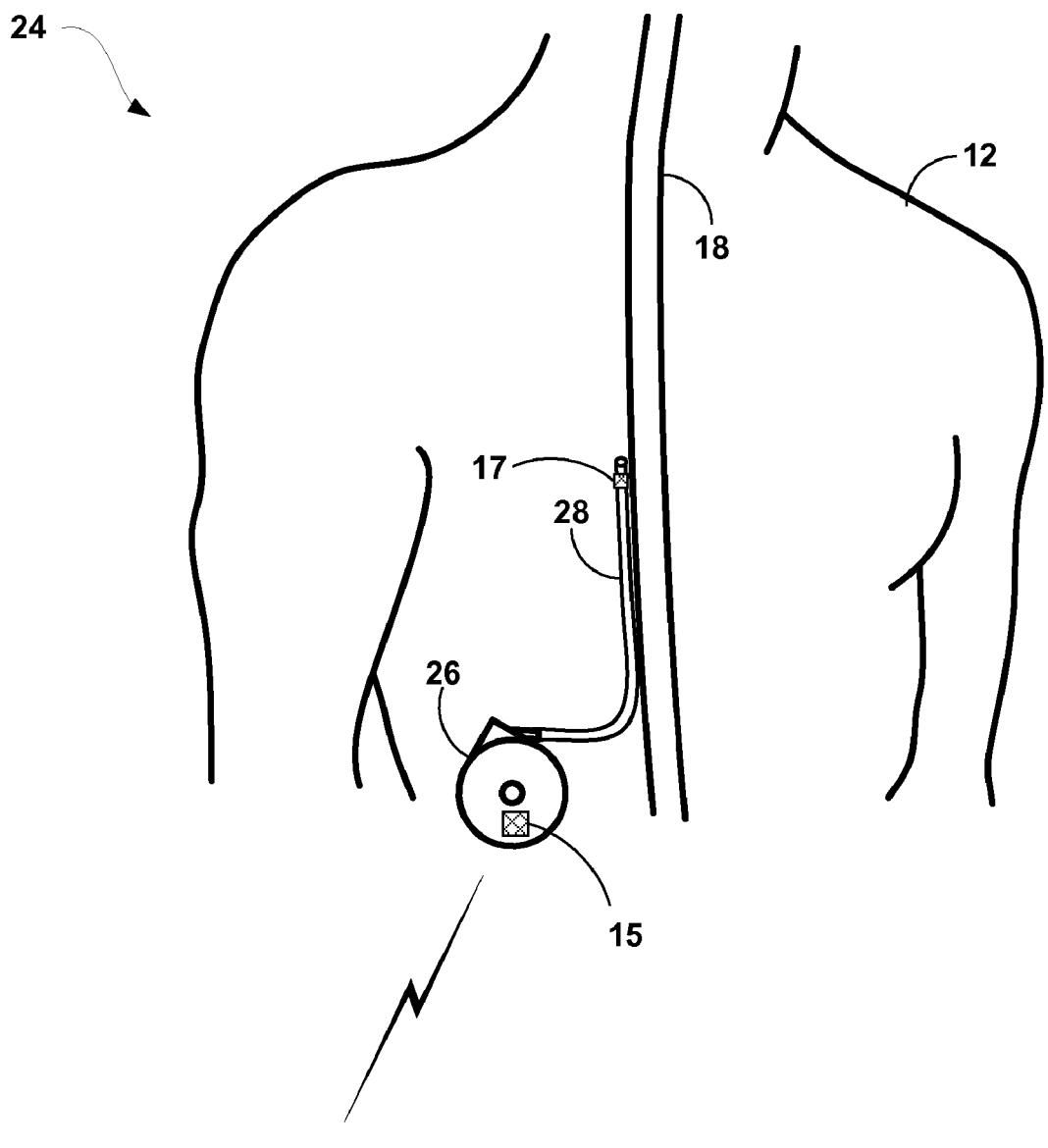
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy, i.e. delivering a therapeutic agent through catheter 28 to patient 12. Example therapeutic agents that IMD 26 may be configured to deliver include, but are not limited to, insulin, morphine, hydromorphone, bupivacaine, clonidine, other analgesics, genetic agents, antibiotics, nutritional fluids, hormones or hormonal drugs, gene therapy drugs, anticoagulants, cardiovascular medications or chemotherapeutics. IMD 26 functions as a drug pump in the example of FIG. 1C, and communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

Catheter 28 may be coupled to IMD 26 either directly or with the aid of a catheter extension (not shown in FIG. 1C). In the example shown in FIG. 1C, catheter 28 traverses from the implant site of IMD 26 to one or more targets proximate to spinal cord 18. Catheter 28 is positioned such that one or more fluid delivery outlets (not shown in FIG. 1C) of catheter 28 are proximate to the one or more target therapy deliver sites within patient 12. In the example of FIG. 1C, IMD 26 delivers a therapeutic agent to targets proximate to spinal cord 18 or nerves that branch from spinal cord 18. IMD 26 may be configured for intrathecal drug delivery into the intrathecal space or epidural delivery into the epidural space both of which surround spinal cord 18. The epidural space (also known as "extradural space" or "peridural space") is the space within the spinal canal (formed by the surrounding vertebrae) lying outside the dura mater, which encloses the arachnoid mater, subarachnoid space, the cerebrospinal fluid, and spinal cord 18. The intrathecal space is within the subarachnoid space, which is past the epidural space and dura mater and through the theca.

Although the target therapy delivery site shown in FIG. 1C is proximate to spinal cord 18 of patient 12, other applications of drug delivery system 24 include alternative target delivery sites. The target delivery site in other applications of drug delivery system 24 may be located within patient 12 proximate to, e.g., sacral nerves (e.g., the S2, S3, or S4 sacral nerves) or any other suitable nerve, organ, muscle or muscle group in patient 12, which may be selected based on, for example, a patient condition. In one such application, drug delivery system 24 may be used to deliver a therapeutic agent to tissue proximate to a pudendal nerve, a perineal nerve or other areas of the nervous system, in which cases, catheter 28 would be implanted and substantially fixed proximate to the respective nerve.

Positioning catheter 28 to deliver a therapeutic agent to various sites within patient 12 enables drug delivery system 24 to assist in managing, e.g., peripheral neuropathy or postoperative pain mitigation, ilioinguinal nerve therapy, intercostal nerve therapy, gastric stimulation for the treatment of gastric motility disorders and/or obesity, and muscle stimulation, or for mitigation of other peripheral and localized pain (e.g., leg pain or back pain). As another example delivery site, catheter 28 may be positioned to deliver a therapeutic agent to a deep brain site or within the heart (e.g., intraventricular delivery of the agent). Delivery of a therapeutic agent within the brain may help manage any number of disorders or diseases including, e.g., depression or other mood disorders, dementia, obsessive-compulsive disorder, migraines, obesity, and movement disorders, such as Parkinson's disease, spasticity, and epilepsy. Catheter 28 may also be positioned to deliver insulin to a patient with diabetes.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Just as with IMD 14, IMD 26 may include a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Also, just as with therapy systems 10 (FIG. 1A) and 22 (FIG. 1B), therapy system 24 includes at least two posture sensors 15, 17 that generate signals indicative of a patient posture state. IMD 26 determines a patient posture state based on input from one of sensors 15, 17 at a time, and adjusts therapy delivery to patient 12 based on the determined posture state in order to accommodate varying conditions patient 12 that may change based on the patient posture state. For example, IMD 26 may control drug delivery to patient 12 based on one or both of patient posture as determined based on input from only one of first posture sensor 15 or second posture sensor 17 at any given time. In some examples, IMD 26 may toggle between the inputs of one of first or second posture sensors 15, 17 based on one or both of a sensed posture state of patient 12 or a sensed status of one or both of posture sensors 15, 17. In other examples, IMD 26 may also use one of first or second posture sensors 15, 17 to automatically reorient the other sensor for one or more posture states of patient 12.

Figure 2:
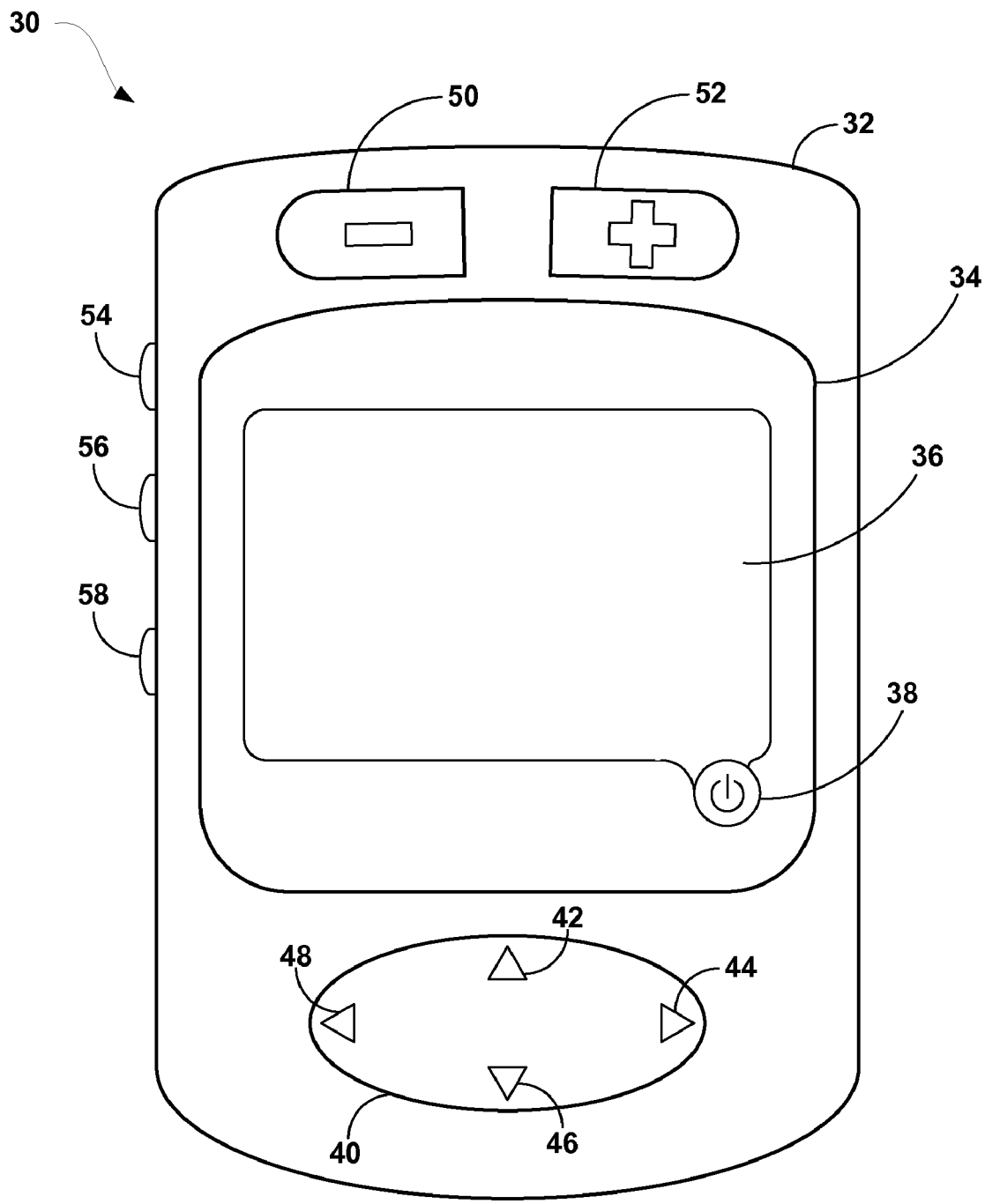
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. Patient programmer 30 is an example embodiment of external programmer 20 illustrated in FIGS. 1A, 1B and 1C and may be used with either IMD 14 or IMD 26. In other examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate. Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein.

Patient programmer 30 also includes display 36, power button 38, increase button 52, decrease button 50, sync button 58, stimulation ON button 54, and stimulation OFF button 56. Cover 34 protects display 36 from being damaged during user manipulation (e.g., interaction) with patient programmer 30. Patient programmer 30 also includes control pad 40, which allows a user to navigate through items displayed on display 36 in the direction of arrows 42, 44, 46, and 48. In some examples, the buttons and control pad 40 take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Patient 12 may control the illumination level, or backlight level, of display 36 by using control pad 40 to navigate through the user interface and increase or decrease the illumination level with decrease and increase buttons 50 and 52 respectively. In some examples, illumination may be controlled by a knob that rotates clockwise and counter-clockwise to control the operational status of patient programmer 30 and the illumination of display 36. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of liquid crystal display (LCD), dot matrix display, organic light-emitting diode (OLED) display, touch screen, or similar monochrome or color display capable of providing visible information to patient 12. Display 36 may provide a user interface regarding current stimulation therapy or posture state information, or provide a user interface for receiving feedback or medication input from patient 12. Display 36 may also present an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication. Display 36 may also present options for a user to manually select one of first and second posture sensor 15, 17, and display operational status of patient programmer 30 or IMDs 14 or 26. For example, patient programmer 30 may provide options for manually instructing IMD 14 to select one of first posture sensor 15 or second posture sensor 17 based on, e.g., the sensed status of the other of first or second posture sensors 15, 17 as failing or otherwise malfunctioning. The selection options displayed by programmer 30 may be any of a number of user interface controls including, e.g., check boxes, drop down lists, or radio buttons or any combination thereof.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In the example of FIG. 2, patient 12 may also use control pad 40 to adjust the volume, display contrast and illumination, time, and measurement units of patient programmer 30. In some examples, pressing the middle of control pad 40 may select any item highlighted items presented on display 36. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy or review posture state information.

Decrease button 50 and increase button 52 provide an input mechanism for patient 12. In general, activation of decrease button 50 may decrease the value of a highlighted stimulation parameter. Buttons 50, 52 may be activated by depressing the respective button. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either button 50 and 52 is selected, patient programmer 30 may initialize communication with IMD 14 or 26 to change therapy accordingly.

When depressed by patient 12, stimulation ON button 54 directs programmer 30 to generate a command that is transmitted to IMD 14, where the command instructs IMD 14 to turn on stimulation therapy. Stimulation OFF button 56 turns off stimulation therapy when depressed by patient 12. Sync button 58 causes patient programmer 30 to communicate with IMD 14 within a substantially minimal amount of time from activation of sync button 58. When patient 12 enters an automatic posture response screen of the user interface, activating sync button 58 (e.g., by pressing sync button 58) turns on the automatic posture response to allow IMD 14 to automatically change therapy according to the posture state of patient 12. Activating sync button 58 again, when the automatic posture response screen is displayed, turns off the automatic posture response. In the example shown in FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
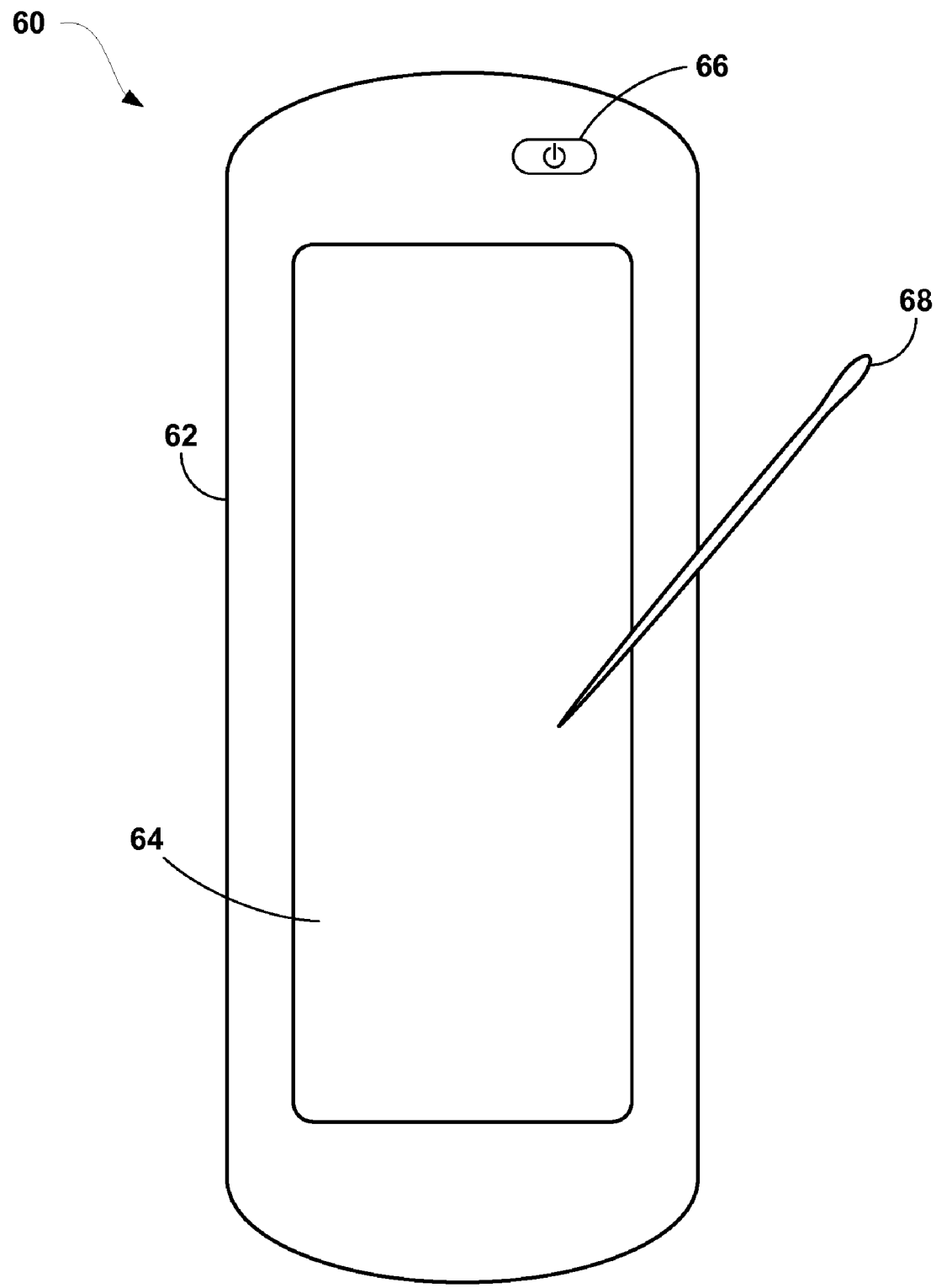
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an implantable medical device. Clinician programmer 60 is an example embodiment of external programmer 20 illustrated in FIGS. 1A, 1B and 1C and may be used with either IMD 14 or IMD 26. In alternative examples, clinician programmer 60 may be used with an external medical device. Clinician programmer 60 provides a user interface (not shown) for a user, such as a clinician, physician, technician, or nurse, to manage and program stimulation therapy. In addition, clinician programmer 60 may be used to review objective posture state information to monitor patient 12 progress and therapy efficacy.

A clinician uses clinician programmer 60 to modify and review therapy to patient 12. With the aid of programmer 60, the clinician may define each therapy parameter value for each of the programs that define stimulation therapy and program IMD 14 or IMD 26 with the selected therapy parameter values. The therapy parameter values, such as amplitude, may be defined specifically for each of the posture states that patient 12 will be engaged in during therapy. In addition, the clinician may use clinician programmer 60 to define each posture state of patient 12 by using the posture state spaces described, e.g. with reference to FIGS. 8A-8C below, or some other technique for associating posture data received from one of first or second posture sensors 15, 17 to the posture state of patient 12.

Clinician programmer 60 includes housing 62, display 64, and power button 66. In the example of FIG. 3, clinician programmer 60 is protected by housing 62, which encloses circuitry necessary for clinician programmer 60 to operate and accommodates display 64 and power button 66. Housing 62 may be constructed of a polymer, metal alloy, composite, or combination material suitable to protect and contain components of clinician programmer 60. In addition, housing 62 may be partially or completely sealed such that fluids, gases, or other elements do not penetrate the housing and affect components therein.

Display 64 is a touch screen that accepts user input via touching certain areas within display 64. The user may use stylus 68 to touch display 64 and select virtual buttons, sliders, keypads, dials, or other such representations presented by the user interface shown by display 64. In some examples, instead of or in addition to stylus 68, the user may touch display 64 with a finger, pen, or any other pointing device. In alternative examples, clinician programmer 60 may include one or more buttons, keypads, control pads, touch pads, or other devices that accept user input, similar to patient programmer 30. Power button 66 may turn clinician programmer 60 ON or OFF as desired by the user. Additionally, clinician programmer 60 may require a password, biometric input, or other security measure to be entered and accepted before a user interacts with the device.

As shown in FIG. 3, clinician programmer 60 is a hand held device. Programmer 60 may be used within the clinic or on in-house patient calls, and to communicate with multiple IMDs 14 and 26 within different patients. In this manner, clinician programmer 60 may be capable of communicating with many different devices and retain and segregate data for more than one patient. Clinician programmer 60 may also take other shapes or sizes not described herein. For example, programmer 60 may take the form of a clam-shell shape, similar to some cellular phone designs. When clinician programmer 60 is closed, at least a portion of display 64 is protected within housing 62. When programmer 60 is opened, on the other hand, one side of the programmer may contain a display while the other side may contain input mechanisms. In some examples, clinician programmer 60 may be a larger, less portable device including, e.g., a notebook computer, workstation, or even a remote computer that communicates with IMD 14 or 26 via a remote telemetry device. In any shape or size, clinician programmer 60 may be capable of performing the requirements described herein.

Most, if not all, of clinician programmer 60 functions may be completed via the touch screen of display 64. The user may program stimulation parameter values, modification profiles, modify therapy programs or groups, retrieve stored therapy data from an IMD or another device, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Clinician programmer 60 may also present information for manually selecting one of first posture sensor 15 or second posture sensor 17 with which IMD 14 or 26 determines a patient posture state. As with patient programmer 30 in FIG. 2, clinician programmer 60 may present selection options to a user (e.g., the clinician) for selecting one of first and second posture sensor 15, 17 based on a variety of conditions. In this way, a clinician may manually instruct IMD 14 through clinician programmer 60 to select one of the multiple posture sensors implanted within patient 12, instead of automatic selection by IMD 14. As described more generally with respect to external programmer 20 in FIG. 1A, in one example, a clinician may, e.g., manually instruct IMD 14 to select one of first posture sensor 15 or second posture sensor 17 based on which of the two will most effectively sense the particular posture state patient 12 is in at the time.

In some cases, all processing is performed in IMD 14 and distributed to clinician programmer 60 only for presentation to the clinician. In other cases, IMD 14, clinician programmer 60, patient programmer 30, or another computing device share in the processing duties of therapy adjustment information and any other data prior to presenting the information on clinician programmer 60.

Figure 4:
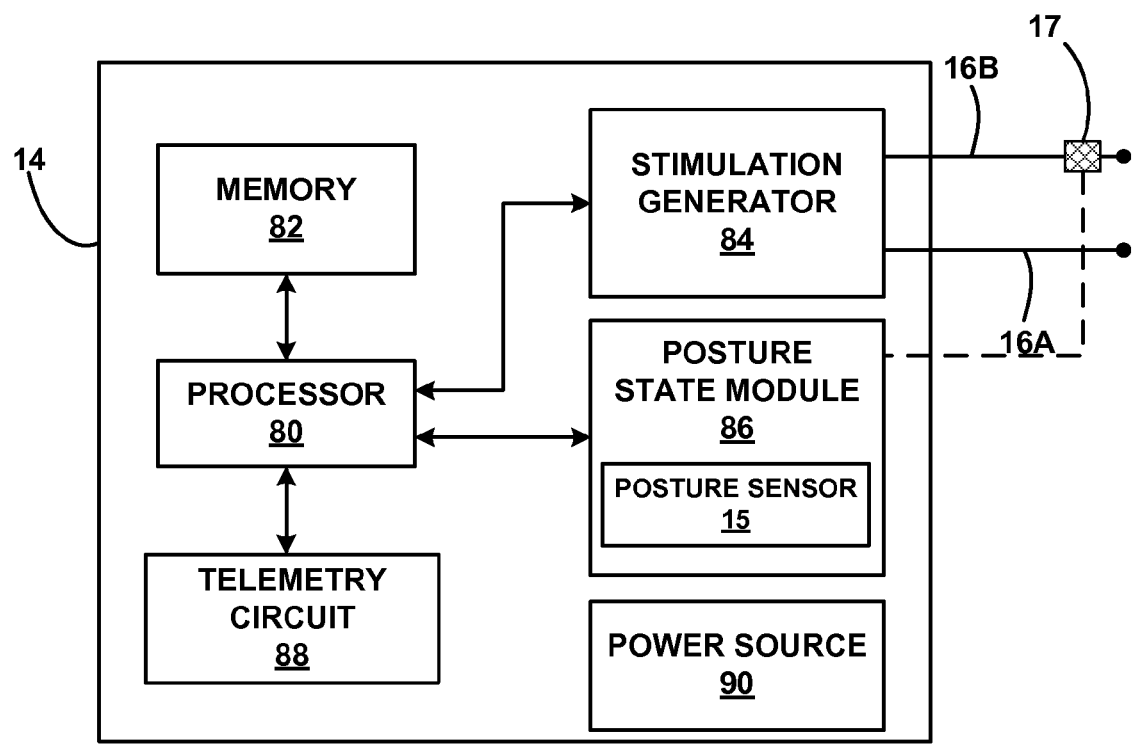
FIG. 4 is a functional block diagram illustrating various components of an implantable electrical stimulator.

FIG. 4 is a functional block diagram illustrating various components of an example IMD 14. In the example shown in FIG. 4, IMD 14 includes a processor 80, memory 82, stimulation generator 84, posture state module 86, telemetry circuit 88, and power source 90. Processor 80 is operably connected to and configured to access information from memory 82 and to control stimulation generator 84, posture state module 86, and telemetry circuit 88. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to IMD 14 may be embodied in a hardware device via software, firmware, hardware or any combination thereof.

Memory 82 may store instructions for execution by processor 80, stimulation therapy data, posture state information (e.g., posture state definitions, information associating posture states with therapy programs, and the like), posture state indications, and any other information regarding therapy of patient 12. Therapy information may be recorded for long-term storage and retrieval by a user, and the therapy information may include any data created by or stored in IMD 14. Memory 82 may include separate memories for storing instructions, posture state information, therapy adjustment information, program histories, and any other data that may benefit from separate physical memory modules. Memory 82 may include any volatile or non-volatile media, such as a random access memory (RAM), read only memory (ROM), non-volatile RAM (NVRAM), electrically erasable programmable ROM (EEPROM), flash memory, and the like.

Stimulation generator 84 forms a therapy delivery module of IMD 14. Processor 80 controls stimulation generator 84 to deliver electrical stimulation via electrode combinations formed by electrodes in one or more electrode arrays. For example, stimulation generator 84 may deliver electrical stimulation therapy via electrodes on one or more of leads 16, e.g., as stimulation pulses or continuous waveforms. Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy is delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 not only accesses the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 detects a posture state transition of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state, e.g. changing from a program appropriate for lying down to a program appropriate for being upright.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.
2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.
3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 Hz to approximately 1200 Hz, such as approximately 5 Hz to approximately 250 Hz, or approximately 30 Hz to approximately 185 Hz, and a pulse width in the range of approximately 10 microseconds and 5000 microseconds, such as between approximately 60 microseconds and approximately 1000 microseconds, between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameter values stored by memory 82, e.g., as therapy programs and groups of programs. Upon selection of a particular program group, processor 80 controls stimulation generator 84 to deliver stimulation according to the programs in the groups, e.g., simultaneously or on a time-interleaved basis. A therapy group may include a single program or multiple programs. As mentioned previously, each therapy program specifies values for a set of stimulation parameters, such as amplitude, pulse width, and pulse rate. In addition, each program may specify a particular electrode combination for delivery of stimulation. Again, the electrode combination may specify particular electrodes in a single array or multiple arrays, e.g., on a single lead or among multiple leads. Processor 80 also controls telemetry circuit 88 to send and receive information to and from external programmer 20 or another computing. For example, telemetry circuit 88 may send information to and receive information from patient programmer 30.

Processor 80 determines a patient posture state based on posture state information from posture state module 86. Posture state information may indicate the patient posture, activity level, or any other static position or motion of patient 12. In the example shown in FIG. 4, posture state module 86 includes two posture sensors 15, 17. First posture sensor 15 is connected to IMD 14, while second posture sensor 17 is connected to electrical lead 16. In alternative examples first and second posture sensors 15, 17 may be located in different positions within patient 12 and relative to components of therapy system 10. For example, first posture sensor 15 may be an independent implantable sensor that is implanted adjacent but physically disconnected from IMD 14. Alternatively, first posture sensor 15 may be worn externally on patient 12 adjacent IMD 14. Second posture sensor 17 may be, e.g., connected to an additional sensor lead positioned within patient 12 adjacent electrical leads 16. Alternatively, second posture sensor 17 may be an independent implantable sensor that is implanted adjacent but physically disconnected from either of leads 16A and 16B. In some examples, second posture sensor 17 is arranged proximate a therapy delivery site within patient 12, while first posture sensor 15 is arranged closer to IMD 14 than first posture sensor 15.

First and second posture sensors 15, 17 may be selected from various sensors appropriate for sensing patient posture and/or activity. For example, one or both of first and second posture sensors 15, 17 may be accelerometers, such as three-axis accelerometers, capable of detecting static orientation or vectors in three-dimensions. Alternatively, posture sensors 15, 17 may include multiple single-axis accelerometers, dual-axis accelerometers, or some combination thereof. Example accelerometers include micro-electro-mechanical accelerometers. In other examples, one or both of first and second posture sensors 15, 17 may include gyroscopes, piezoelectric crystal, pressure transducers or other sensors to sense the posture state of patient 12. Posture state information generated by posture state module 86 and processor 80 may correspond to posture state undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12, or some combination thereof. As an example, processor 80 may record the posture state parameter value, or output, of one of first or second posture sensors 15, 17 and assign the posture state parameter value to a certain predefined posture indicated by the posture state parameter value. In this manner, IMD 14 may track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

As described herein, the posture state data, or raw data of the posture state information, is stored to be later used. The posture state information may also be used in addition to the therapy adjustment information when the user desires to view more detailed information related to the posture states engaged by patient 12. Memory 82 may store all of the posture state data detected during therapy or use of IMD 14, or memory 82 may periodically offload the posture state data to clinician programmer 60 or a different external programmer 20 or device. In other examples, memory 82 may reserve a portion of the memory to store recent posture state data easily accessible to processor 80 for analysis. In addition, older posture state data may be compressed to require less memory until later needed by external programmer 20 or processor 80.

A posture state parameter value from posture state module 86 that indicates the posture state may vary constantly throughout the day of patient 12. However, a certain activity (e.g., walking, running, or biking) or a posture (e.g., standing, sitting, or lying down) may include multiple posture state parameter values from posture state module 86. Memory 82 stores definitions for each posture state of patient 12. In one example, the definitions of each posture state may be illustrated as a cone in three-dimensional space, although other types of posture state regions are contemplated. Examples of posture cones are described below with reference to FIGS. 8A-8C. Whenever the posture state parameter value, e.g., a vector, from one of first posture sensor 15 or second posture sensor 17 of posture state module 86 resides within a predefined cone, processor 80 indicates that patient 12 is in the posture state associated with that cone. In other examples, processor 80 (or a separate processor of posture state module 86) compares a posture state parameter value from one of first or second posture sensors 15, 17 to a look-up table or equation to determine the posture in which patient 12 currently resides.

Posture-responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters may be tedious, requiring patient 14 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

In other embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state.

In some embodiments, processor 80 processes the analog output of one of first or second posture sensors 15, 17 in posture state module 86 to determine activity and/or posture data. For example, where one of first or second posture sensors 15, 17 comprises an accelerometer, processor 80 may process the raw signals provided by one of first or second posture sensors 15, 17 to determine activity counts. In some embodiments, processor 80 may process the signals provided by one of first or second posture sensors 15, 17 to determine velocity of motion information along each axis.

In one example, each of the x, y, and z signals provided by one of first or second posture sensors 15, 17 has both a DC component and an AC component. The DC components describes the gravitational force exerted upon the sensor and may thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion. This activity may involve a level, direction of motion, or acceleration of the patient.

One method for determining the activity is an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count." The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

In order to facilitate the delivery of efficacious posture-responsive therapy to patient 12, IMD 14 is configured to determine a patient posture state based on input from one of at least two posture sensors 15, 17 of a therapy system. Processor 80 may adjust therapy delivery by stimulation generator 84 based on the determined posture states to accommodate the varying conditions patient 12 encounters in a variety of posture states during use of therapy system 10. Processor 80 of IMD 14 may control therapy delivery to patient 12 based on one or both of patient posture or activity level as determined based on input from only one of first posture sensor 15 or second posture sensor 17 at any given time. In some examples, processor 80 may toggle between activating first posture sensor 15 connected to IMD 14 and deactivating second posture sensor 17 connected to electrical stimulation lead 16A, and deactivating first posture sensor 15 and activating second posture sensor 17. In other examples, posture sensors 15, 17 may be simultaneously active, but IMD 14 may selectively receive input from only one of the sensors. In this way, the processor may toggle between receiving posture state input from, as opposed to activating one of first or second posture sensors 15, 17. Several conditions may occur during delivery of therapy to patient 12 that affect or dictate which one of first posture sensor 15 and second posture sensor 17 processor 80 of IMD 14 selects for determining a patient posture state. In some examples, processor 80 toggles to one of first and second posture sensors 15, 17 based on the sensed posture state of patient 12. In other examples, processor 80 toggles to one of first and second posture sensors 15, 17 based a sensed status of the other of first and second posture sensors 15, 17. Toggling to one of the sensors 15, 17 includes, e.g., activating one of the sensors for detecting posture state and receiving posture state input from one of the sensors.

As patient 12 receives posture-responsive therapy from IMD 14 over a period of time, various conditions may make one of first and second posture sensors 15, 17 more effective in providing data related to different posture states of patient 12. For example, migration of the posture sensor or the component to which the sensor is attached may make one of the output from one of first or second posture sensors 15, 17 more accurate than the other in certain posture states. In the event IMD 14 is implanted in the buttocks of patient 12, e.g., the device may be particularly susceptible to movement when patient 12 is sitting. In such a case, first posture sensor 15 may be less suited to sense the posture state of patient 12 than second posture sensor 17, which remains substantially unaffected by the posture. Therefore, processor 80 may toggle to second posture sensor 17 while patient 12 is sitting.

The selection of one of first and second posture sensors 15, 17 based on the posture state of patient 12 may be based on associations stored in memory 82 of IMD 14. For example, a clinician and/or patient 12 may use patient programmer 30 and/or clinician programmer 60 to associate first posture sensor 15 with some posture states of patient 12 and second posture sensor 17 with the remaining posture states of patient 12.

In addition to selecting one of the two posture sensors 15, 17 of a therapy system based on a particular posture state, processor 80 may select one of the sensors 15, 17 with which to determine a patient posture state based on the status of the other sensor. An example technique for selecting one of the two posture sensors 15, 17 based on the status of one of the sensors 15, 27 is described with reference to FIG. 12. In some examples, processor 80 of IMD 14 monitors the status of one or both first and second posture sensors 15, 17 for, e.g., malfunctions, failures, inaccurate or incomplete data, or the like. In one example, processor 80 may monitor first and second posture sensors 15, 17 and select one of the sensors in the event the other fails. In this way, first and second posture sensors 15, 17 provide a redundant motion sensing system with a primary and a backup sensor.

As described with reference to FIG. 12, in some examples, processor 80 monitors first and second posture sensors 15, 17 and selects one of the sensors for detecting the patient posture state in the event the other sensor becomes disoriented. In still another example, processor 80 may monitor first and second posture sensors 15, 17 and select one of the sensors in the event the other sensor inaccurately measures a posture state of patient 12. Inaccurate posture state measurements may be detected by comparing posture data received from first and second posture sensors 15, 17 to one another and may be caused by, e.g., movement of one of the sensors in a particular posture state of patient 12 or one of the sensors losing a posture state orientation.

With reference to FIG. 4, the selection of first or second posture sensor 15, 17 has been described as controlled by IMD 14, and, in particular by processor 80 of IMD 14. However, as described above with reference to FIGS. 2 and 3, first and second posture sensor 15, 17 may also or exclusively be manually selected by patient 12 and/or a clinician using one or both of patient programmer 30 and clinician programmer 60. In other examples, a processor of one of programmers 30, 60 may automatically select a posture sensor 15, 17 with which a therapy system determines a patient posture state. Accordingly, while processor 80 of IMD 14 is primarily referred to herein as selecting one of posture sensors 15, 17 for detecting a patient posture state, in other examples, a processor of one of programmers 30, 60 or another device may perform any part of the techniques described herein.

In addition to selectively receiving posture state input from one of first or second posture sensors 15, 17, IMD 14 may also use one of first or second posture sensors 15, 17 to automatically reorient the other of first or second posture sensors 15, 17 for one or more posture states of patient 12. An example technique processor 80 may implement in order to reorient a posture sensor 15, 17 is described with reference to FIG. 14. In some instances a posture sensor, such as sensors 15, 17, may become disoriented relative to the body of patient 12. Disorientation of one of first or second posture sensors 15, 17 may occur in situations in which the physical location of the posture sensor changes with respect to the patient. Because the other of the first or second posture sensors 17 remains in a more stable position within patient 12, e.g., due to the nature of the surrounding tissue or the region of the body of the patient in which the sensor is implanted, the more stable sensor may be used to automatically reorient the disoriented sensor. In some examples, one of the posture sensors may be implanted in softer to tissue than the other, which may make the posture sensor in the softer tissue more likely to move. As another example, one of the multiple posture sensors of therapy system 10 may be implanted in a region of the body of patient 12 that is undergoes more movement (e.g., near a joint or spine of patient 12) than the region in which another posture sensor is located.

In some examples, processor 80 of IMD 14 may detect the disorientation of first posture sensor 15 based on a failure of first posture sensor 15 to correctly indicate a first posture state of patient 12. IMD 14 may be configured to utilize typical patient posture state behavior over a period of time, e.g., daily, weekly, etc., to determine if it is likely that one of first or second posture sensors 15, 17 has been disoriented. For example, IMD 14 may be configured to store data relating to patient posture states over a period of time in memory 82 and employ processor 80 to analyze the historical data to recognize typical periods of time that patient 12 is, e.g. sleeping and, thus, should be occupying one or more lying down posture states. If processor 80 determines that the posture state of patient 12 detected by one of first or second posture sensors 15, 17 at those times is not a lying posture state, then IMD 14 may take suitable action, such as initiating an automatic reorientation procedure in accordance with examples disclosed herein.

As another example, IMD 14 may monitor patient posture state and store posture states of patient 12 over a period of time. Processor 80 may then analyze the historical posture state data to determine one or more patterns of patient behavior or activity over time. If processor 80 detects a posture state or a series of posture states that are not consistent with the determined pattern, then IMD 14 may again take an appropriate action such as automatic reorientation. As another example, IMD 14 may be configured to monitor for sensor disorientation using input from patient 12. Patient 12 may periodically communicate with IMD 14, e.g., via patient programmer 30 (FIG. 3) to identify a posture state that patient 12 is currently occupying or is about to occupy. Processor 80 of IMD 14 may verify that the posture state detected using one of first or second posture sensors 15, 17 is consistent with the state indicated by patient 12. Such a technique may be used, e.g., when patient 12 is about to lie down to sleep, lies down, is about to stand up or is standing up.

All of these examples of detecting the disorientation of one of first or second posture sensors 15, 17 for a posture state of patient 12 may be augmented or replaced by comparing posture data received from one of first or second posture sensors 15, 17 to posture data received from the other of first or second posture sensors 15, 17. In such cases, processor 80 may analyze posture data from both of first and second posture sensors 15, 17 to determine if sensors 15, 17 are providing inconsistent posture data, which may in turn indicate the disorientation of one of the sensors. Comparing posture data from first and second posture sensors 15, 17 may be performed by processor 80 on a substantially continuous basis, or may be implemented periodically based on other indicators including, e.g., when one of the other techniques described herein for detecting posture sensor disorientation indicates a potential orientation issue with one of first or second posture sensors 15, 17.

Once IMD 14 detects the disorientation of one of first or second posture sensors 15, 17, processor 80 may interrogate the other sensor to determine the posture state patient 12 actually occupies by receiving posture data indicative of the posture state of patient 12, i.e. indicative of which one of a plurality of posture states is the first posture state. Processor 80 may then reorient the one of first or second posture sensors 15, 17 for the first posture state without any interaction from patient 12 or a clinician. For example, processor 80 may reorient one of first or second posture sensors 15, 17 by interrogating the sensor for posture data relating to the first posture state of patient 12. Processor 80 may then define posture reference data based at least in part on the posture data received from the one of first or second posture sensors 15, 17. The posture reference data may be used by processor 80 to define a reoriented spatial posture region that corresponds to the first posture state, which may be stored in memory 82. Having reoriented the one of first or second posture sensors 15, 17 for the first posture state, IMD 14 may then seamlessly continue to deliver posture-responsive therapy to patient 12 in the first posture state by comparing posture data from the reoriented sensor to the newly defined posture region. Posture regions, including, e.g., posture cones will be described in greater detail with reference to FIGS. 8A-8C, 13A and 13B below.

Wireless telemetry in IMD 14 with external programmer 20, e.g., patient programmer 30 or clinician programmer 60, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
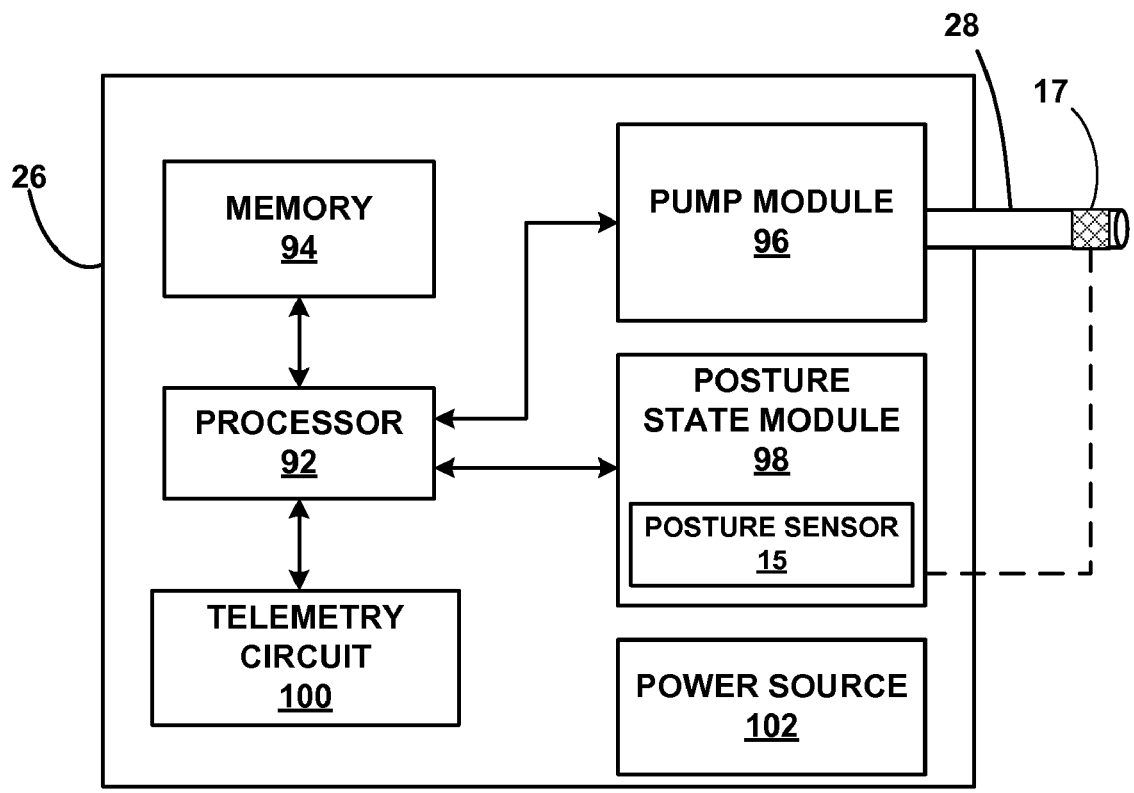
FIG. 5 is a functional block diagram illustrating various components of an implantable drug pump.

FIG. 5 is a functional block diagram illustrating various components of an example IMD 26 that delivers a therapeutic agent to a target therapy delivery site within patient 12. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96, which delivers drugs or some other therapeutic agent via catheter 28. Pump module 96 may include a reservoir to hold the drug and a pump mechanism to force drug out of catheter 28 and into patient 12. Posture state module 98 of IMD 26 includes first posture sensor 15 connected to IMD 26 and second posture sensor 17 connected to catheter 28.

Processor 92 may control pump module 96 according to therapy instructions stored within memory 94. For example, memory 94 may contain the programs or groups of programs that define the drug delivery therapy for patient 12. A program may indicate various parameters of the therapeutic agent delivery, such as the bolus size or flow rate of the drug, and processor 92 may accordingly deliver therapy. Processor 92 may also use posture state information from posture state module 98 to adjust drug delivery therapy when patient 12 changes posture states, e.g., transitions between postures. Additionally, and similar to IMD 14, processor 92 may control therapy delivery to patient 12 based on one or both of patient posture as determined based on input from only one of first posture sensor 15 or second posture sensor 17 at any given time in order to accommodate varying conditions patient 12 encounters in a variety of posture states during use of therapy system 10.

Figure 6:
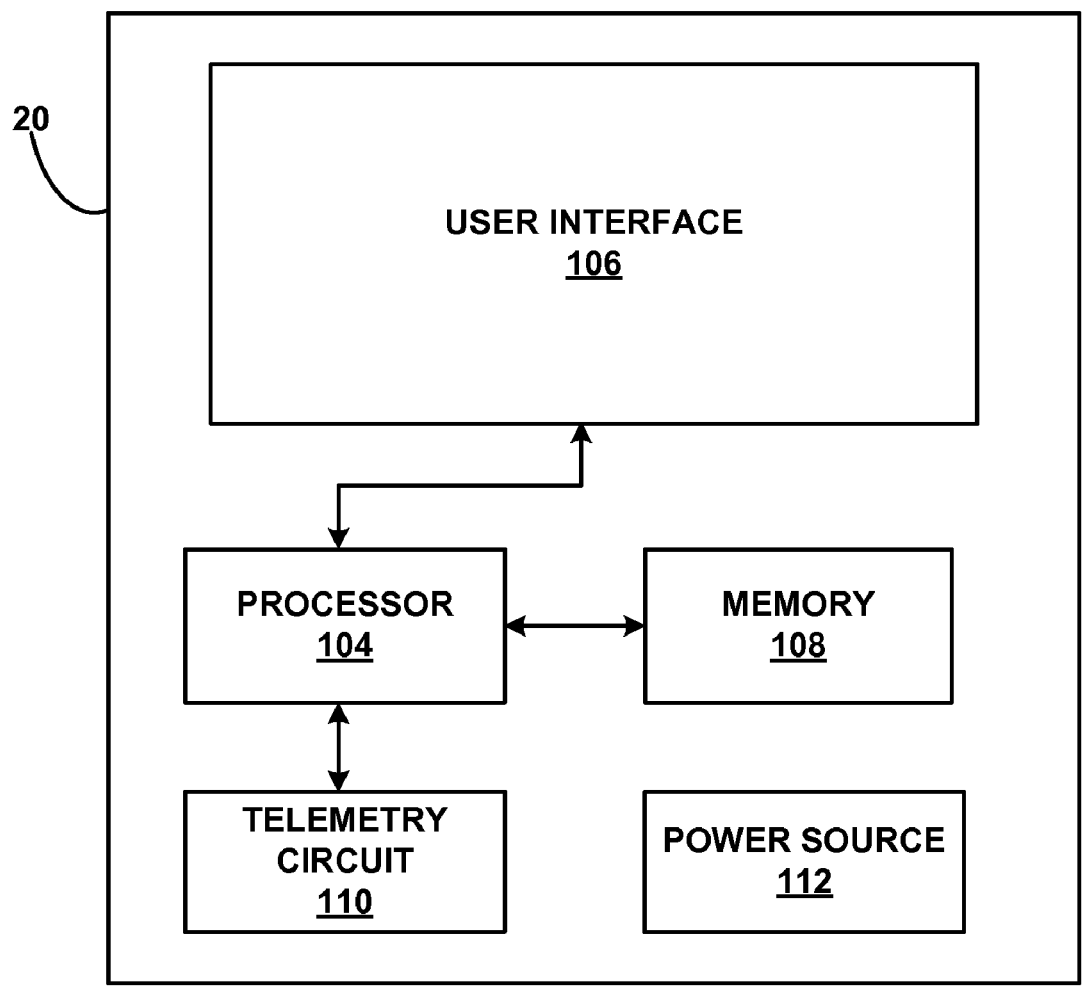
FIG. 6 is a functional block diagram illustrating various components of an external programmer for an implantable medical device.

FIG. 6 is a functional block diagram illustrating various components of an external programmer 20 for IMDs 14 (FIG. 4) or 26 (FIG. 6). As shown in FIG. 6, external programmer 20 includes processor 104, user interface 106, memory 108, telemetry circuit 110, and power source 112. External programmer 20 may be embodied as patient programmer 30 or clinician programmer 60. A clinician or patient 12 interacts with user interface 106 in order to manually change the stimulation parameters of a program, change programs within a group, turn posture-responsive stimulation ON or OFF, view therapy information, view posture state information, manually select one of first or second posture sensors 15, 17, or otherwise communicate with IMDs 14 or 26.

User interface 106 may include a screen and one or more input buttons, as in the example of patient programmer 30, that allow external programmer 20 to receive input from a user. Alternatively, user interface 106 may additionally or exclusively utilize a touch screen display, as in the example of clinician programmer 60. The screen may be a LCD, dot matrix display, OLED display, touch screen, or any other device capable of presenting and/or accepting information.

Input mechanisms for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

In some examples in which patient 12 is permitted to manually adjust one or more therapy parameter values, user interface 106 presents therapy adjustment information to the user for monitoring adjustments made by patient 12 in different posture states. The therapy adjustment information may be stored within memory 108 of external programmer 20 periodically during therapy, whenever external programmer 20 communicates with IMD 14, or only when the user desired to use the therapy adjustment information. Memory 108 may include a separate memory for therapy adjustment information as opposed to other posture state information or operational instructions. In addition, if memory 108 does store posture state information from patient 12, memory 108 may use one or more hardware or software security measures to protect the identify of patient 12. For example, memory 108 may have separate physical memories for each patient or the user may be required to enter a password to access each patient's posture state data.

Processor 104 may present options to a user via user interface 106 for selecting one of first and second posture sensor 15, 17 for use by IMD 14 for monitoring a patient posture state. Patient 12, e.g., may manually select a desired first or second posture sensor 15, 17 through interaction with user interface 106 for the current posture state of patient 12. Alternatively, a clinician and/or patient 12 may use interface 106 to permanently or semi-permanently associate first posture sensor 15 with particular posture states of patient 12 and second posture sensor 17 with other posture states of patient 12.

Associations between one of first or second posture sensors 15, 17 and particular posture states may be used to improve detection of patient posture states because, e.g., the location of first and second posture sensors 15, 17 within patient 12 may make the sensors more or less effective for sensing different posture states of patient 12. For example, if IMD 14 is implanted in the upper buttocks of patient 12, IMD 14 may be subject to more movement when patient 12 is sitting compared to when patient 12 is standing. In such a case, the patient posture state indicated by the signal from first posture sensor 15, which is connected to IMD 14, may be inaccurate or incorrect due to the migration of IMD 14 within patient 12 while sitting. Processor 80 can therefore, e.g., "confirm" the detected posture state based on second posture sensor 17, which was previously associated with the posture state in the manner described. The associations may be stored in memory 82 of IMD 14 and processor 80 may then automatically select one of first or second posture sensors 15, 17 based on the associations. After the associations between first and second posture sensors 15, 17 and the posture states of patient 12 have been stored in memory 82 of IMD 14, user interface 106 of external programmer 20 may present the associations to the user in a variety of formats including, e.g., a table listing which of first and second posture sensor 15, 17 is associated with which posture state of patient 12.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like.

Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. In other examples, a separate recharging device may be employed that is capable of communication with IMD 14. Then, the recharging device can, in addition to charging IMD 14, transfer programming information, data, or any other information described herein to IMD 14. In this manner, the recharging device may act as an intermediary communication device between external programmer 20 and IMD 14. The techniques described herein may be communicated between IMD 14 via any type of external device capable of communication with IMD 14.

Figure 7:
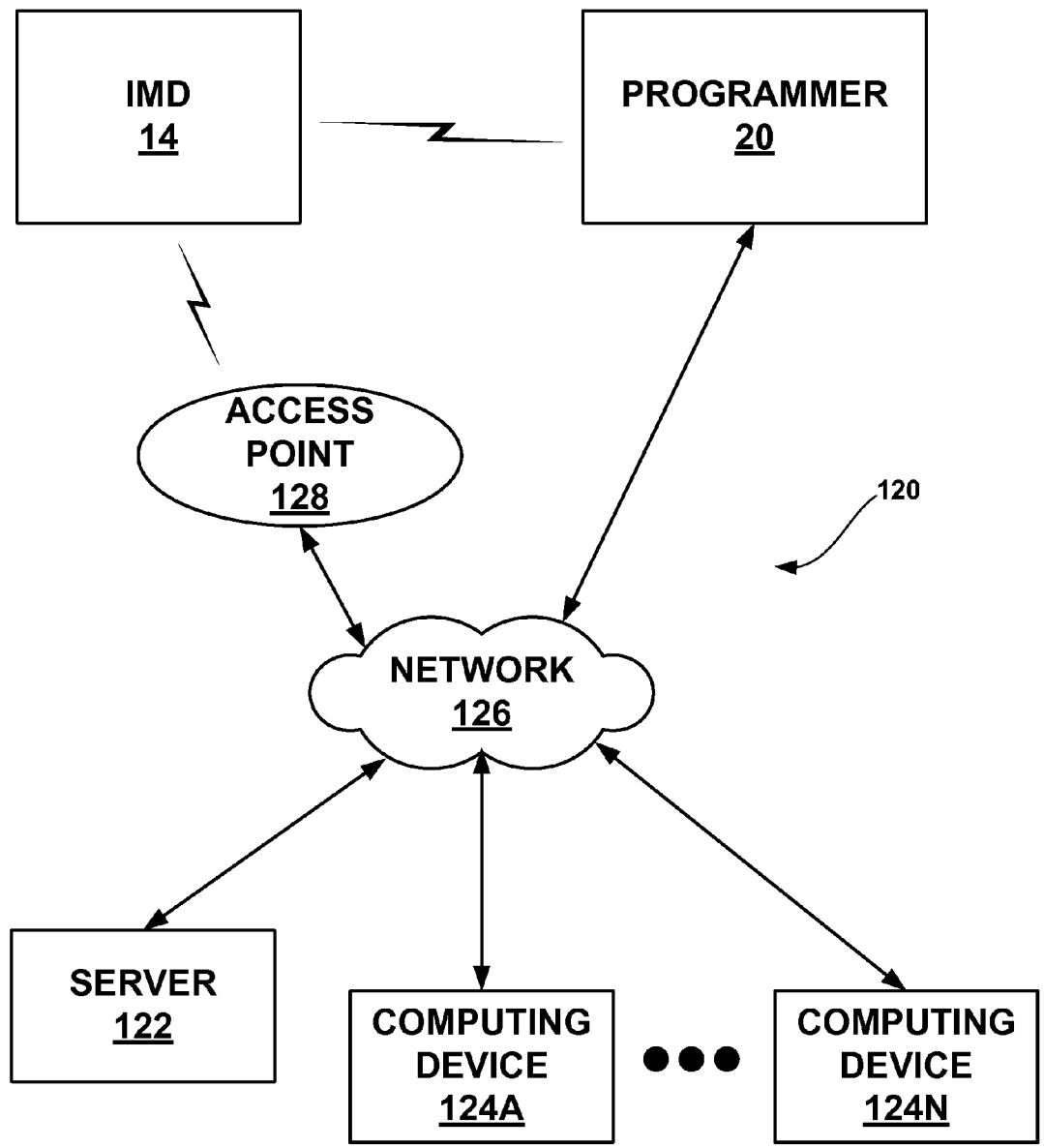
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and/or external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day and track any manual or automatic toggling between first and second posture sensors 15, 17. IMD 14 may also process, trend and evaluate the sensed posture state and posture sensor selection information. In some cases, IMD 14 may directly analyze the collected data to, e.g., evaluate the posture state of patient 12, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. In such cases, processing, trending and evaluation functions may be distributed to these other devices such as external programmer 20 or server 122.

Communication between IMD 14 and external devices may occur via network 126 in real time. Network 126 may allow a remote clinician to review the current patient posture state or a remote technician to be alerted to posture sensor malfunctions of failures by receiving a presentation of such information on a remote display, e.g., computing device 124A. In addition, posture state and posture sensor information may be archived by any of these devices to facilitate, e.g., later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, which of first or second posture sensor 15, 17 was active at different times and for different postures, any detected malfunctions or disorientations of one of first or second posture sensors 15, 17 and in which posture state the malfunction occurred, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In the manner of FIG. 7, a clinician, physician, technician, or even patient 12, may review therapy adjustment and other posture state information from IMD 14. The user may remotely monitor the progress and trends of patient 12, limiting the number of times that patient 12 may need to physically visit the clinician. This monitoring may also reduce the time needed to find efficacious therapy parameters by allowing the clinician to more frequently monitor how patient 12 is using patient programmer 30 and how often changes to therapy must be made. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors, such as a malfunction of one of first and second posture sensor 15, 17 to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although system 120 is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
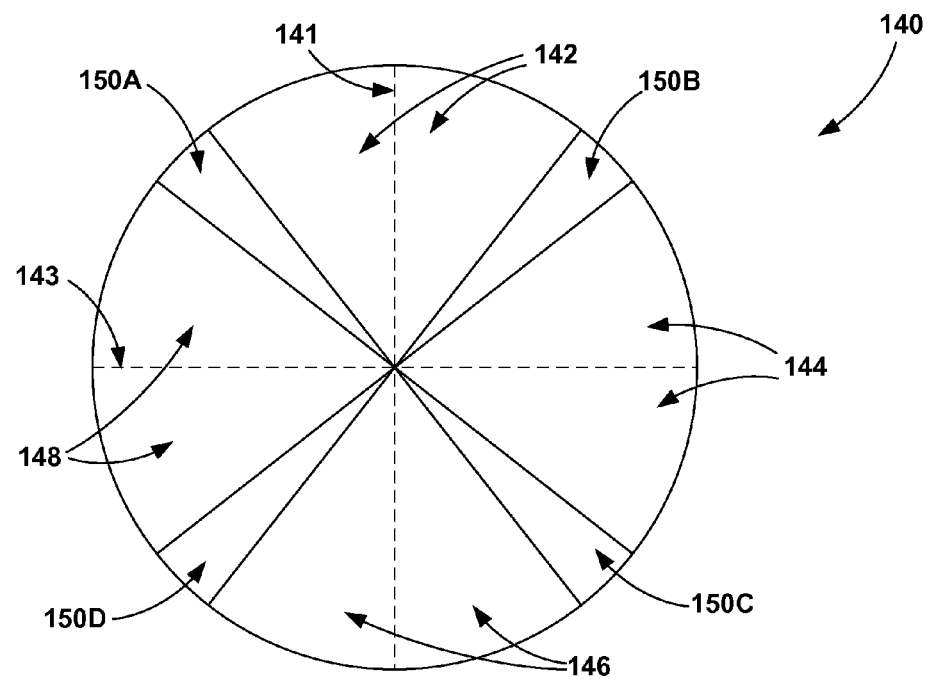
FIGS. 8A-8C are conceptual illustrations of example posture state spaces, which may be used to define the posture state of a patient based on signals generated by a posture sensor.
Figure 8B:
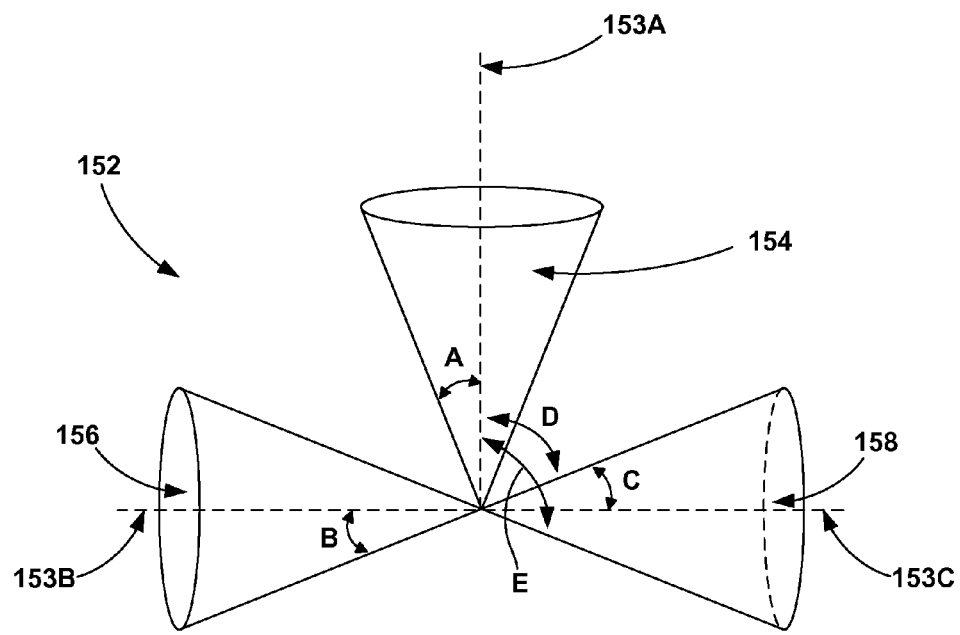
Figure 8C:
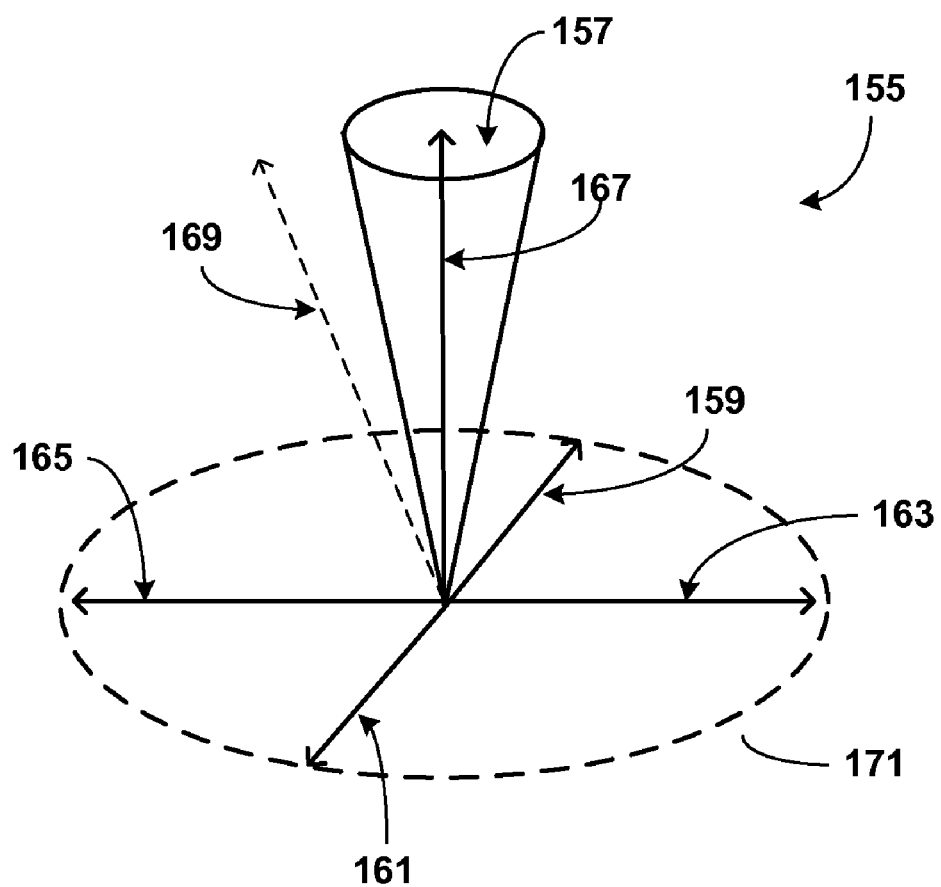

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or both of first and second posture sensors 15, 17 may be analyzed by posture state module 86 with respect to posture state spaces 140, 152, 155 to determine the posture state of patient 12. For example, if the output of one of first or second posture sensors 15, 17 is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use one of first or second posture sensors 15, 17 to sense posture vectors. In some examples, one or more of first and second posture sensors 15, 17 is a three-axis accelerometer that provides data indicating the posture state of patient 12. A sense vector may be determined based on the output of the posture state sensor. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of one of first or second posture sensors 15, 17 may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state area 140 is segmented into different posture cones that are indicative of a certain posture state of patient 12. In the example of FIG. 8A, upright cone 142 indicates that patient 12 is sitting or standing upright, lying back cone 148 indicates that patient 12 is lying on his (or her) back, lying front cone 144 indicates that patient 12 is lying on his chest, and inverted cone 146 indicates that patient 12 is in an inverted position. Other cones may be provided, e.g., to indicate that patient 12 is lying on their right side or left side. Vertical axis 141 and horizontal axis 143 are provided as orientation of posture state area 140.

In some examples, processor 80 of IMD 14 monitors the posture state parameter value of one of first or second posture sensors 15, 17 and identifies the current posture state of patient 12 by identifying the cone in which the posture state parameter value of one of the sensors 15 or 17 resides. For example, if the posture state parameter value falls within lying front cone 144, IMD 14 determines that patient 12 is lying on his chest. IMD 14 may store this posture information, change therapy based on the determined patient posture state, or both. Additionally, IMD 14 may communicate the posture information to patient programmer 30 so that the patient programmer may present a posture state indication to patient 12.

In addition, posture state area 140 includes hysteresis zones 150A, 150B, 150C, and 150D (collectively "hysteresis zones 150"). Hysteresis zones 150 are positions within posture state area 140 in which no posture cones have been defined. Hysteresis zones 150 may be particularly useful when IMD 14 utilizes the posture state information and posture cones to adjust therapy automatically. If one of first or second posture sensors 15, 17 indicates that patient 12 is in upright cone 142, IMD 14 does not detect that patient 12 has entered a new posture cone until the posture state parameter value falls within a different posture cone. For example, if IMD 14 determines that patient 12 moves to within hysteresis zone 150A from upright cone 142, IMD 14 retains the posture as upright. In this manner, processor 80 of IMD 14 does not change the corresponding therapy until patient 12 fully enters a different posture cone. Hysteresis zones 150 prevent IMD 14 from continually oscillating between different therapies when the patient posture state resides around a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by one of first or second posture sensors 15, 17 while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by one of first or second posture sensors 15, 17 at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from one of first or second posture sensors 15, 17 is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of one of first or second posture sensors 15, 17 or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by one of first or second posture sensors 15, 17 of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the signal from one of first or second posture sensors 15, 17 are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one of first or second posture sensors 15, 17 of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other space. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of one of first or second posture sensors 15, 17 of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the In some examples, to detect the posture state of a patient, posture state module 86 of IMD 14 may determine a sensed coordinate vector based on the posture sensor data generated by one of first or second posture sensors 15, 17, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E' may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one of first or second posture sensors 15, 17 while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 86 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 86 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest of the four cosine values, the sensed vector may be considered closest in proximity to lying front reference vector out of the four total reference vectors 159, 161, 163, 165. Accordingly, posture state module 86 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
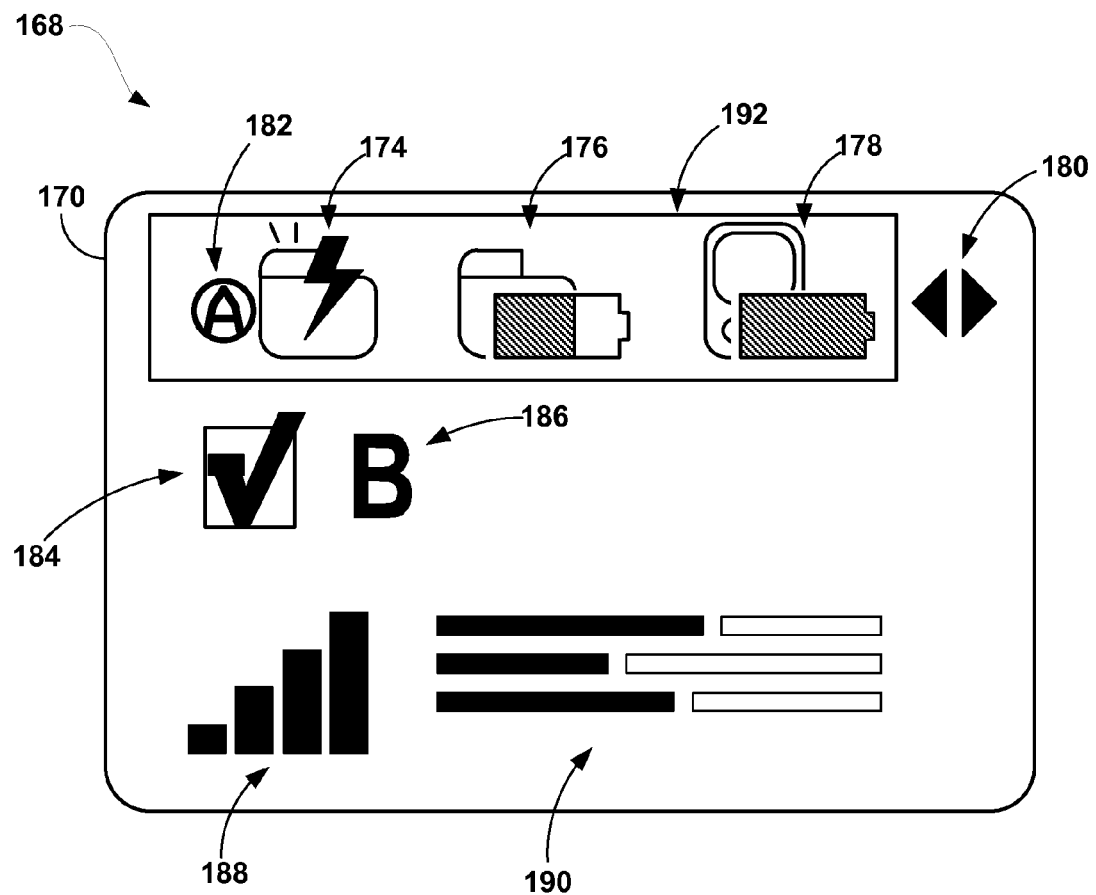
FIG. 9 is a conceptual diagram illustrating an example user interface of a patient programmer that delivers therapy information to the patient.

FIG. 9 is a conceptual diagram illustrating an example user interface 168 of a patient programmer 30 for delivering therapy information to patient 12. In other examples, a user interface similar to user interface 168 may also be shown on clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example of screen 170 shown in FIG. 9, selection box 192 is positioned so that patient 12 may use navigation arrows 180 via arrows 44 and 48 of control pad 40 (shown in FIG. 2) to move to the automatic posture response screen, the volume screen, the contrast or illumination screen, the time screen, and the measurement unit screen of patient programmer 30. In these screens, patient 12 may control the use of the automatic posture response feature and adjust the patient programmer 30 features. Patient 12 may only adjust the features surrounded by selection box 192.

Group identifier 186 indicates one of possibly several groups of programs that may be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of each program's amplitude may be shown in addition to or in place of amplitude graph 190. In other examples of user interface 168 specific to, e.g., drug delivery using IMD 26, amplitude graph 190 may show the flow rate of drugs or frequency of bolus delivery to patient 12. This information may be show in numerical format as well. Patient 12 may encompass group selection icon 184 with selection box 192 and use navigation arrows 180 via arrows 44 and 48 of control pad 40 to scroll between the different programs of the selected group.

Automatic posture response icon 182 indicates that a posture responsive therapy mode of IMD 14 is activated, such that processor 80 (FIG. 4) of IMD 14 automatically adjusts therapy to patient 12 based upon the posture state detected by posture state module 86 (FIG. 4). In particular, when the posture responsive therapy mode of IMD 14 is activated, processor 80 may automatically adjust therapy delivery to patient 12 based on a detected patient posture by adjusting one or more therapy parameter values, selecting different programs or selecting different program groups based on the detected posture state of patient 12. In addition, processor 80 automatically selects one of first and second posture sensor 15, 17 to detect patient posture at a particular time or for particular postures. In the example shown in FIG. 9, automatic posture response icon 182 is not present next to group identifier 186. Therefore, group "B" does not have automatic posture-responsive therapy activated for any of the programs within group "B."

Some groups or individual programs in groups may support automatic posture-responsive therapy. For example, automatic adjustment of one or more therapy parameters in response to posture state indication may be selectively activated or deactivated based on settings entered by a clinician, or possibly patient 12. Hence, some programs or groups may be configured for use with posture-responsive therapy while other programs or groups may not be configured for use with posture-responsive therapy. In some cases, if posture-responsive therapy supported by the automatic posture response feature is desired, patient 12 may need to switch therapy to a different group that has automatic posture-responsive therapy activated for IMD 14.

Figure 10:
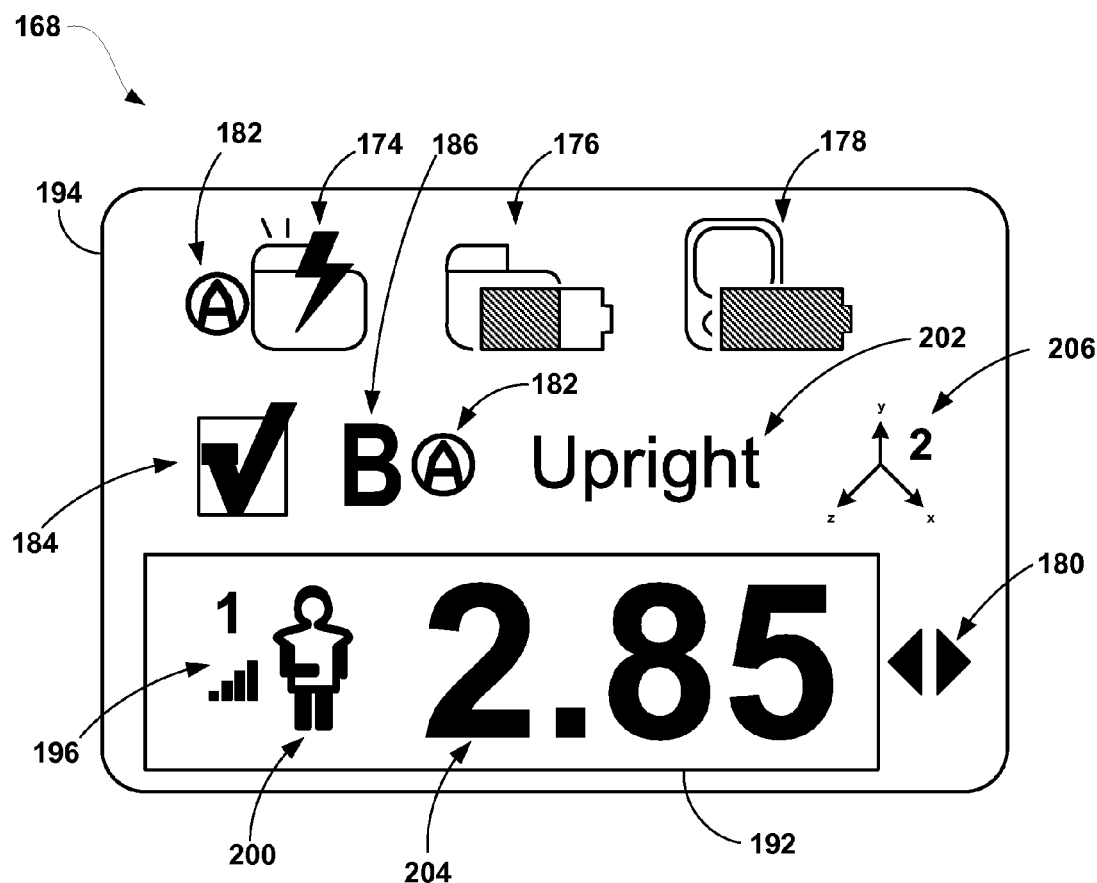
FIG. 10 is a conceptual diagram illustrating an example user interface of a patient programmer that delivers therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Just as with screen 170 of FIG. 9, screen 194 presents stimulation icon 174, IMD battery icon 176, programmer battery icon 178, and automatic posture response icon 182. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding a therapy group, therapy program, stimulation amplitude, automatic posture response status (e.g., an indication of whether the posture responsive therapy mode of IMD 14 is activated), and posture state information. More or less information may be provided to patient 12, as desired by the clinician or the patient.

Group identifier 186 indicates that group "B" is active, and automatic posture response icon 182 indicates group "B" (containing one or more programs) is activated to allow IMD 14 to automatically adjust therapy according to the patient 12 posture state. In the example shown in FIG. 10, user interface 168 indicates the posture state determined by IMD 14, e.g., via posture state indication 200 and supplementary posture state indication 202. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40 (shown in FIG. 2).

Posture state indication 200 shows that IMD 14 is detecting that patient 12 is in the upright or standing posture. Supplementary posture state indication 202 supplements posture state indication 200 by providing a textual indication of the exact posture being detected by posture state module 86 of IMD 14. Posture state indication 200 and supplementary posture state indication 202 change according to the sensed, or detected, posture state detected by IMD 14. The posture state may be communicated to the external programmer immediately when IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 is viewing other programs within group "B" using selection arrows 208. Selection box 192 may be moved to select other screen levels with control pad 40 in order to navigate through other stimulation groups or adjustable elements of the therapy. When patient 12 selects a different program with control pad 40, program identifier 196 will change number to correctly identify the current program viewed on screen 194.

Whether selected automatically by IMD 14 or manually by patient 12 or a clinician, posture sensor icon 206 indicates that second posture sensor 17 is active to sense that patient 12 is currently in the "Upright" posture state. In FIG. 10, patient 12 (or any other user) may select posture sensor icon 206 with selection box 192 and use navigation arrows 180 via arrows 44 and 48 of control pad 40 (FIG. 2) to select one of first and second posture sensors 15, 17 to control the posture sensor 15, 17 with which processor 80 of IMD 14 determines a posture state. In other examples, instead of automatic selection by IMD 14, patient 12 (or any other user) may select posture sensor icon 206 with selection box 192 and use navigation arrows 180 via arrows 44 and 48 of control pad 40 (FIG. 2) to select one of first or second posture sensors 15, 17 to control the posture sensor with which processor 80 of IMD 14 reorients the other of first and second posture sensors 15, 17. For example, patient 12 or another user (e.g., a clinician) may select the posture sensor that is expected to be less likely to change orientation to be the posture sensor that is used to reorient the other posture sensor. Processor 80 of IMD 14 controls therapy delivery based on the posture state determined by the selected first or second posture sensor 15, 17. In some cases, patient 12 manually selects one of first or second posture sensors 15, 17 because, e.g., although user interface 168 indicates that patient 12 is in an "Upright" posture state, patient 12 is actually lying down. In this case, the one of first and second posture sensors 15, 17 that is currently used by IMD 14 to detect the patient posture state may be malfunctioning in some way and is, therefore, detecting the incorrect posture state of patient 12.

Patient 12 may at least temporarily remedy this posture sensor issue by manually activating the one of first and second posture sensors 15, 17 without the malfunction. In other examples, IMD 14 may also or exclusively automatically control selection of one of first or second posture sensors 15, 17 at any given time. IMD 14 can, for example, toggle to one of first or second posture sensors 15, 17 based on the particular posture state of patient 12. In still another example, IMD 14 may toggle to one of first or second posture sensors 15, 17 based on the status of the other of the two sensors including, e.g., where one of the sensors malfunctions, fails, loses a posture state orientation, or measures a posture state inaccurately.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile (or somatosensory) indication may be, for example, different numbers of vibratory pulses delivered in sequence or vibratory pulses of different lengths, amplitudes, or frequencies.

Figure 11:
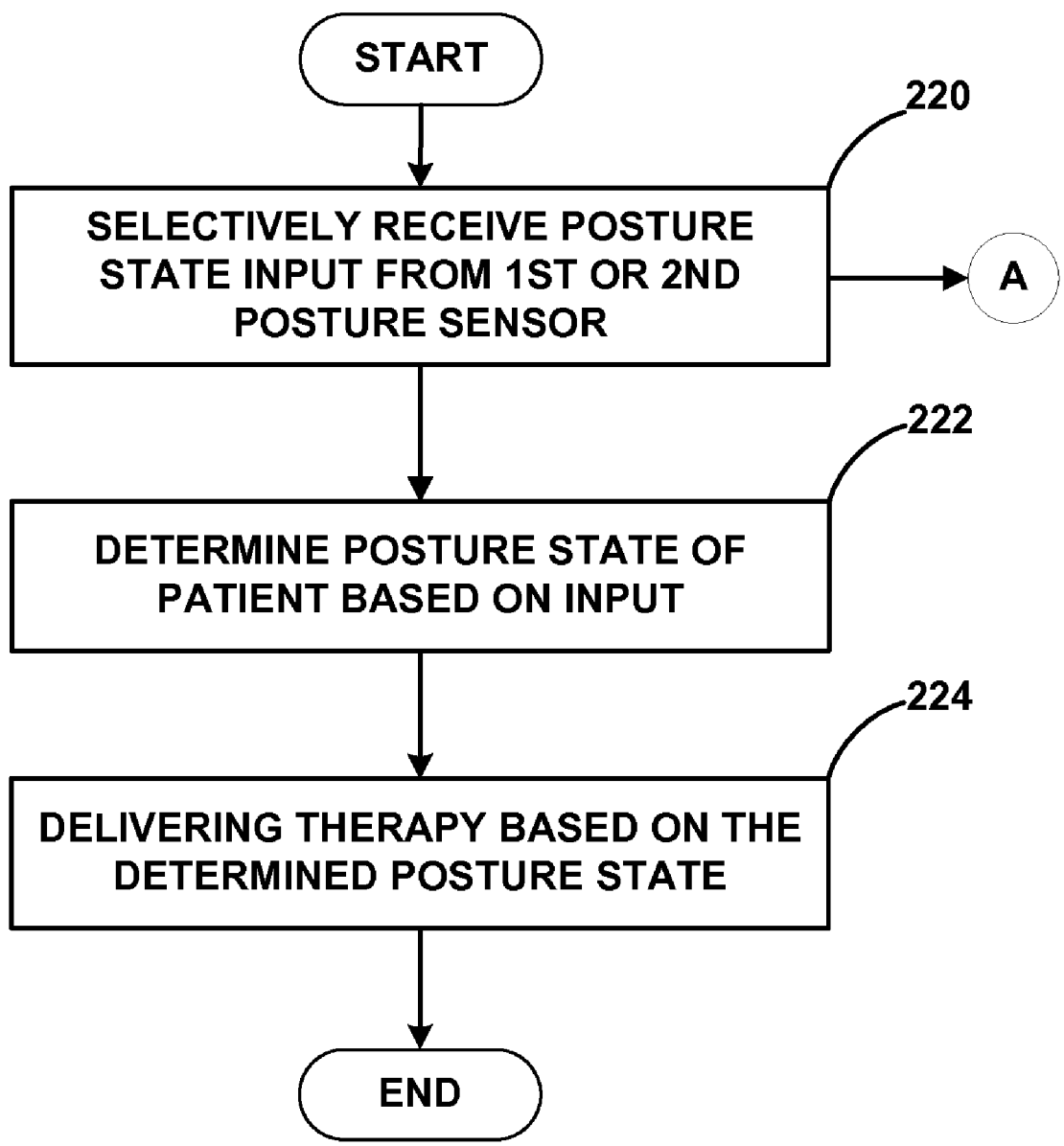
FIGS. 11 and 12 are flow charts illustrating an example method of delivering therapy with an implantable medical system.

FIG. 11 is a flow chart illustrating an example method of delivering therapy with an implantable medical system, such as therapy system 10 (FIG. 1A), therapy system 22 (FIG. 1B), or therapy system 24 (FIG. 1C). While therapy system 10 is primarily referred to throughout the description of FIGS. 11-14, in other examples, other therapy systems, such as therapy systems 22 or 24, may implement the example techniques described herein. In the technique shown in FIG. 11, processor 80 of IMD 14 selectively receives input from one of a first posture sensor 15 or a second posture sensor 17 that is indicative of a posture state of a patient (220), determines the posture state of patient 12 based on the input from one of first or second posture sensors 15, 17 (222), and delivers therapy to patient 12 based on the posture state determined (224). One or both of the first posture sensor and the second posture sensor is implanted within the patient.

The technique shown in FIG. 11, as well as other examples according to this disclosure may be implemented using, e.g., processor 80 of IMD 14 shown in FIG. 4 to execute one or more algorithms stored in memory 82. Similarly, examples disclosed herein may be implemented using processor 92 of IMD 26 shown in FIG. 5 to execute one or more algorithms stored in memory 94.

As described above with reference to various components of therapy system 10, processor 80 of IMD 14 is configured to selectively receive input from one of first posture sensor 15 or second posture sensor 17 that is indicative of a posture state of a patient (222) at any given time to accommodate varying conditions patient 12 encounters in a variety of posture states during use of therapy system 10. As further illustrated in the flow chart of FIG. 12, processor 80 toggles between determining a patient posture state based on input from first posture sensor 15 or second posture sensor 17 (226) based on one or both of the posture state of patient 12 (228) and the status of one of the posture sensors 15, 17 (230).

As IMD 14 delivers posture responsive therapy to patient 12 over a period of time, various conditions may cause one of first or second posture sensors 15, 17 to more accurately provide data indicating different posture states of patient 12. For example, as a result of migration of one of posture sensors 15, 17 or the component to which the sensor is attached, one of first or second posture sensors 15, 17 may more accurately indicate certain posture states than the other posture sensor. Based on the accuracy of a particular posture sensor for indicating a particular posture state of patient 12, each of first and second posture sensors 15, 17 may be associated with one or more of a plurality of posture states for patient 12.

In practice, a clinician and/or patient 12 can, e.g., use patient programmer 30 and/or clinician programmer 60 to associate first posture sensor 15 with some posture states of patient 12 and second posture sensor 17 with other, different posture states of patient 12. In different examples, the clinician or patient 12 may use different criteria for associating a posture sensor to a particular posture state. In some examples, the clinician may associate first and second posture sensors 15, 17 to particular postures based on standards related to the location of the sensors. For example, any posture sensor connected to IMDs implanted within a buttock of patient 12 may be ineffective in detecting a sitting posture. In this case, the clinician may associate second posture sensor 17 connected to lead 16 with the sitting posture state of patient 12.

In other examples, the clinician or patient 12 may manually observe the effectiveness of each of first or second posture sensors 15, 17 in detecting posture states as patient 12 progressively transitions between the postures. For example, patient 12 may progressively occupy different posture states at the prompting of the clinician, who simultaneously observes whether either of first or second posture sensors 15, 17 is detecting the postures correctly using, e.g., visual indications from user interface 168 (FIG. 10). In these ways, processor 80 may toggle to one of first or second posture sensors 15, 17 not only based on the posture state of patient 12 (228), in general, but based on associations between each of the motions sensors and particular posture states of patient 12. For example, in FIG. 12, processor 80 confirms a patient posture state based on second posture sensor 17 when either first or second posture sensors 15, 17 indicate patient 12 is standing or lying down, and processor 80 confirms a patient posture state based on first posture sensor 15 when either first or second posture sensors 15, 17 indicate patient 12 is sitting. Thus, in some cases, processor 80 makes an initial patient posture state determination based on one or both sensors 15, 17 and subsequently determines a final posture state based on the posture sensor 15, 17 associated with the initial patient posture state in order to, e.g., confirm the posture state prior to controlling therapy delivery based on the determined posture state.

In addition to selectively determining a patient posture state based on input from one of first or second posture sensors 15, 17 depending on a particular posture state (228), processor 80 may toggle to one of the posture sensors based on the status of the other sensor (230). That is, processor 80 may selectively determine the posture state of patient 12 that controls therapy delivery based on input from one of sensors 15, 17 (230). As illustrated in FIG. 12, IMD 14 may be configured to monitor the status of both of first and second posture sensors 15, 17 for one or more of, e.g., malfunctions, failures, inaccurate or incomplete data, or the like.

In one example, IMD 14 monitors first and second posture sensors 15, 17 and processor 80 selectively determines a patient posture state based on one of the sensors 15, 17 in the event the other posture sensor fails. In other examples, IMD 14 monitors first and second posture sensors 15, 17 and processor 80 selectively determines a patient posture state based on one of the sensors in the event the other sensor loses a posture state orientation. In still another example, IMD 14 monitors first and second posture sensors 15, 17 and processor 80 selectively determines a patient posture state based on one of the sensors in the event the other sensor inaccurately measures a posture state of patient 12. Inaccurate posture state measurements may be detected by comparing data received from first and second posture sensors 15, 17 to one another and may be caused by movement of one of the sensors within patient 12 in a particular posture state or by one of the sensors losing a posture state orientation.

Figure 12:
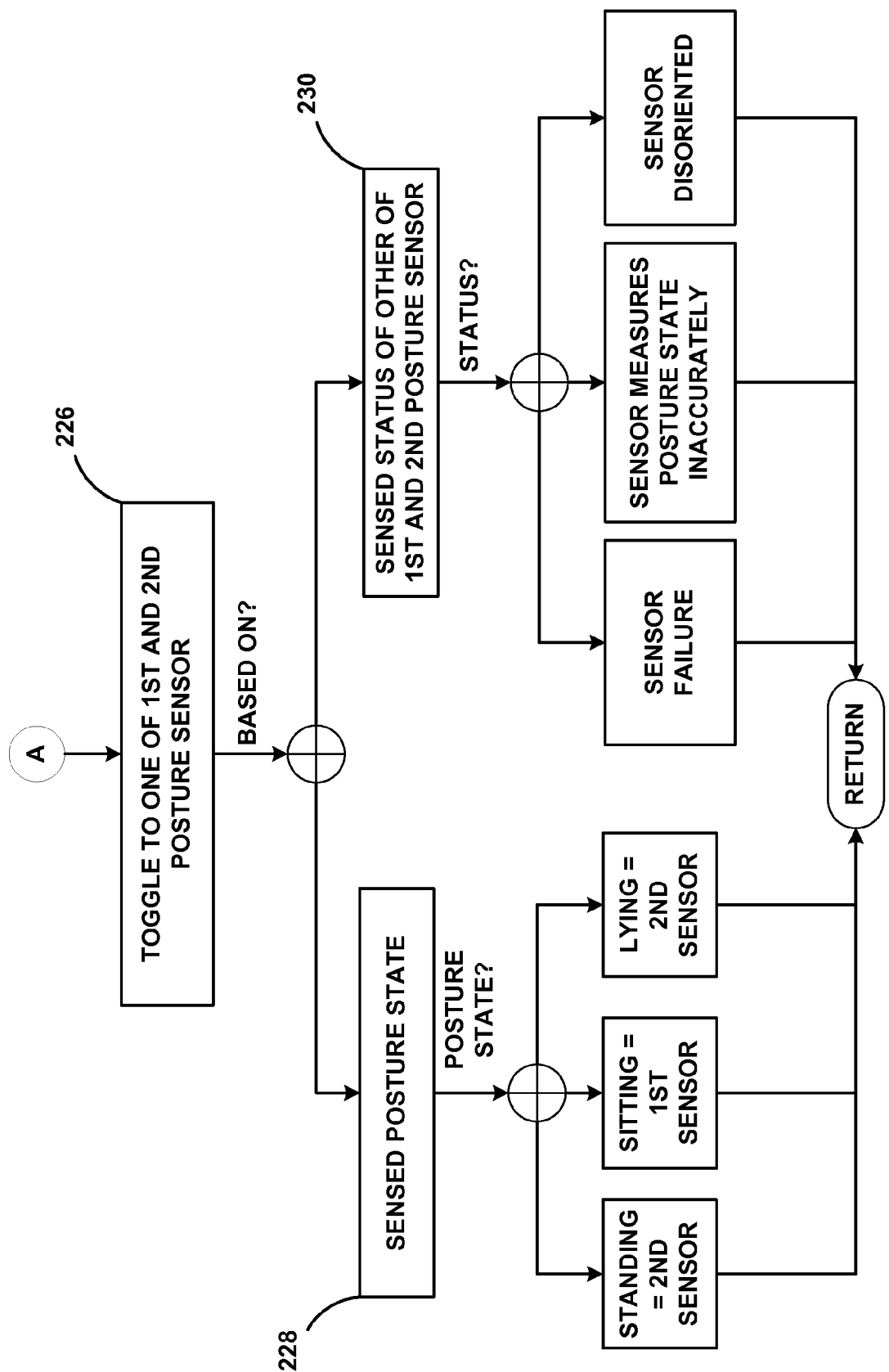

In examples including the features illustrated in FIG. 12, after processor 80 selects to receive input from either the first or second posture sensor 15, 17 (226) based on patient posture state (228) and/or the status of one of the sensors (230), processor 80 determines the posture state of patient 12 based on the posture sensor input received from the one of first or second posture sensors 15, 17 to which the processor toggled (222) and IMD 14 delivers therapy to patient 12 based on the posture state of patient 12 determined by processor 80 (224) as illustrated in FIG. 11.

With reference to FIGS. 11 and 12, receiving input from one of first or second posture sensors 15, 17 has been described as controlled by IMD 14, and, in particular by processor 80 of IMD 14. However, as described above with reference to FIGS. 2 and 3, first and second posture sensor 15, 17 may also or exclusively be manually toggled to by patient 12 and/or a clinician using one or both of patient programmer 30 and clinician programmer 60.

In addition to selectively receiving input from only one of first or second posture sensors 15, 17, one of the posture sensors may also be employed by IMD 14 to automatically reorient the other sensor for one or more posture states in the case of sensor disorientation.

Figure 13A:
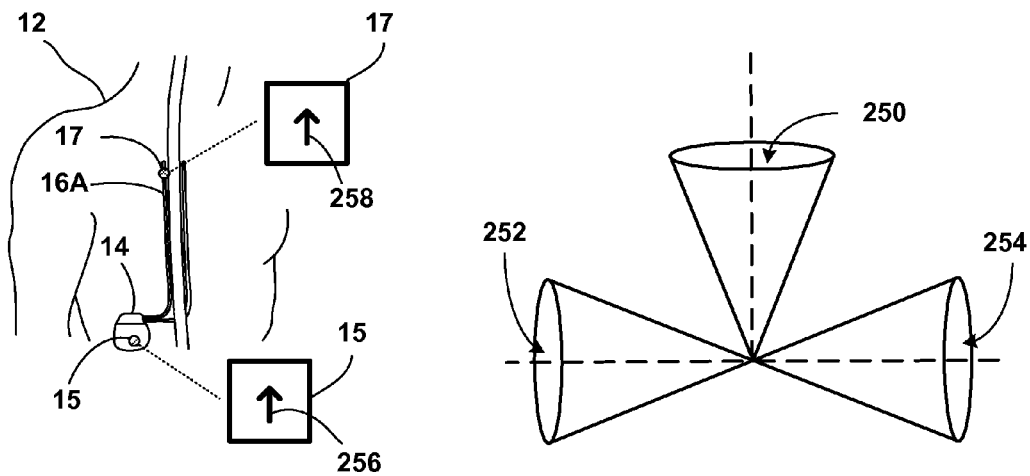
FIGS. 13A and 13B are conceptual illustrations of example posture cones used to define one or more posture states of a patient.
Figure 13B:
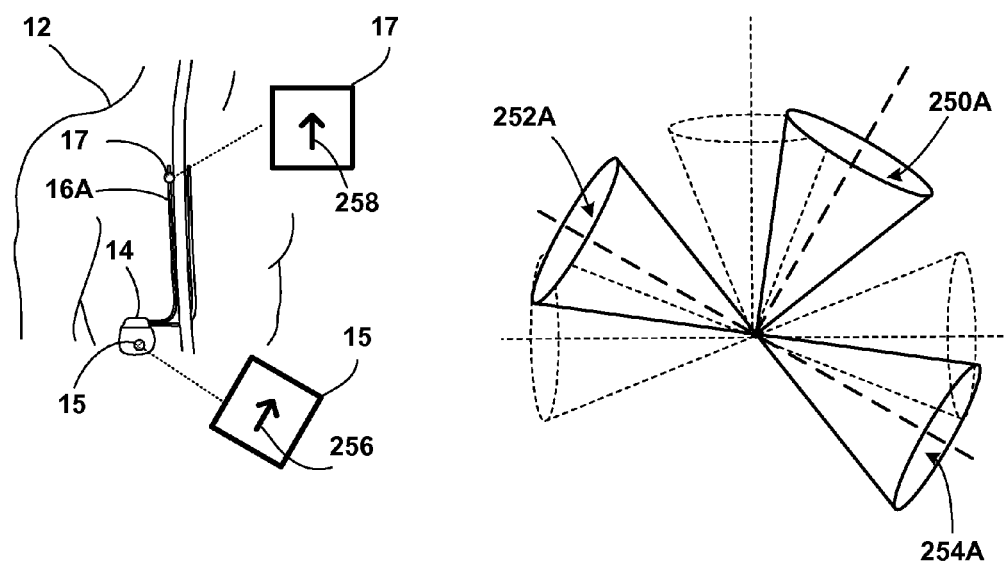

FIGS. 13A and 13B are conceptual illustrations of example posture cones used to define one or more posture states of patient 12 based on posture data from one of first or second posture sensors 15, 17, and the respective orientations of first and second posture sensors 15, 17 under varying conditions encountered by patient 12. FIGS. 13A and 13B illustrate how the movement of one of first or second posture sensors 15, 17 within patient 12 may cause the sensor to become disoriented for a particular posture state, e.g., an "upright" posture state as shown in FIGS. 13A and 13B. As previously mentioned, postures cones may represent a type of posture reference data used by an IMD to detect the posture state occupied by a patient. Similar to posture cones 154, 156, and 158 of FIG. 8B, posture cones 250, 252, and 254 exist in a three-dimensional posture space and define one or more posture states of patient 12 by associating signals from one of first or second posture sensors 15, 17 with a particular posture state. In the example of FIG. 13A, posture cones 250, 252, and 254 indicate patient posture states of "upright," "lying right," and "lying left," respectively. However, in another example, posture cones 250, 252, 254 could also indicate patient posture states of "upright," "lying front," and "lying back" respectively. In addition, as described with respect to FIG. 8C, in some examples, posture states may be defined by an upright posture cone and one or more reference coordinate vectors for one or more lying down posture states.

As described above with respect to electrical stimulation therapy systems 10 and 22, and drug delivery system 24 in FIGS. 1A-1C respectively, first and second posture sensors 15, 17 may be part of a posture state module included in an IMD, such as posture state module 86 (FIG. 4) of IMD 14. For purposes of illustration, automatic reorientation of one of first or second posture sensors 15, 17 will be described with reference to IMD 14 of therapy system 10. However, the techniques described may also be applied to other arrangements including, e.g., therapy system 22 and drug delivery system 24 of FIGS. 1B and 1C respectively.

IMD 14 and medical leads 16 are implanted in patient 12 at, e.g., the relative location indicated in FIGS. 13A and 13B. First posture sensor 15 is connected to IMD 14 and may include, e.g., a three-axis accelerometer, the signal of which may be analyzed by IMD 14 to detect the posture state of patient 12. For example, first posture sensor 15 may be enclosed within an outer housing of IMD 14 or may be otherwise connected to the housing, such that when the housing of IMD 14 moves, posture sensor 15 moves. Second posture sensor 17 is connected to medical lead 16A and may also include, e.g., a three-axis accelerometer, the signal of which may be analyzed by IMD 14 to detect the posture state of patient 12.

After implantation of IMD 14, leads 16, and first and second posture sensors 15, 17 within patient 12, processor 80 of IMD 14 determines one or more posture states of patient 12 using posture reference data based at least in part on posture data from one of first or second posture sensors 15, 17 and posture cones 250, 252, and 254. During a programming session, a clinician may define posture cones 250, 252, 254 with the aid of clinician programmer 60 or programmer 60 may automatically determine posture cones 250, 252, 254. IMD 14 provides posture-responsive therapy to patient 12 by modifying stimulation therapy being delivered to patient 12 based on the posture state detected by IMD 14 using posture cones 250, 252, and 254. For ease of illustration, to show the physical orientation of sensors 15, 17 with respect to patient 12 in FIGS. 13A and 13B, sensors 15, 17 are also shown outside of patient 12 and include reference arrows 256 and 258 to indicate the orientation of each of first and second posture sensors 15, 17 respectively.

Postures cones 250, 252, and 254 may be defined based on one or more of the characteristics of posture data produced by one of first or second posture sensors 15, 17 while patient 12 occupies each of the respective posture states indicated by posture cones 250, 252, and 254. The posture data may include, e.g., x, y, z coordinates from which a sense vector may be derived and compared to a posture cone defined by, e.g., a reference coordinate vector and a tolerance value including, e.g., a distance, angle, or range of cosine values defining a range of coordinate vectors within a cone surrounding the reference coordinate vector. For example, upright posture cone 250 may be defined based on one or more characteristics of the posture data (e.g., a vector) from one of first or second posture sensors 15, 17, which form posture reference data, while patient 12 occupies an upright posture state. Each posture cone 250, 252, and 254 may be defined using such a process after IMD 14 and leads 16, including first and second posture sensors 15, 17, are implanted in patient 12. In this manner, each of the posture cones 250, 252, and 254 may be defined based on the characteristics of the posture data generated by one or both of posture sensors 15, 17 when patient 12 is known to occupy the posture state associated with the respective posture cone 250, 252, 254, and when first or second posture sensors 15, 17 are known to be in a particular orientation relative to patient 12.

In the example shown in FIG. 13A, posture cones 250, 252, and 254 are defined for patient 12 when each of first and second posture sensors 15, 17 are physically oriented as shown in FIG. 13A. FIG. 13A also illustrates that the relative space occupied by each of posture cones 250, 252, and 254 is the three-dimensional posture space used to define the posture states of patient 12. Using posture cones 250, 252, and 254, IMD 14 may detect the posture state of patient 12 by comparing the posture data received from one of first or second posture sensors 15, 17 to the space defined by each posture cone 250, 252, and 254.

As previously mentioned, in some instances a posture sensor, such as sensors 15, 17, may become disoriented relative to the body of patient 12 after posture reference data defining the posture cones 250, 252, 254 have already been obtained. Disorientation of one of first or second posture sensors 15, 17 may occur in situations in which the physical location of the posture sensor changes with respect to patient 12. As explained above, the location of first and second posture sensors 15, 17 within patient 12 may make each of the sensors 15, 17 more or less effective for sensing different posture states of patient 12. In some examples, IMD 14 is implanted in the upper buttocks of patient 12, which makes IMD 14 susceptible to movement relative to an initial orientation when patient 12 is in certain posture states, such as sitting. In such a case, first posture sensor 15 may become disoriented when patient 12 is engaged in a sitting posture state due to the migration of IMD 14 and, therefore, posture sensor 15 within patient 12. This and other examples are schematically illustrated in FIG. 13B, which illustrates a situation in which the physical orientation of first posture sensor 15 with respect to patient 12 is different than that of the physical orientation of sensor 15 with respect to patient 12 in FIG. 13A. In particular, although patient 12 occupies substantially the same posture in FIGS. 13A and 13B, arrow 256 indicates that first posture sensor 15 has changed orientations with respect to patient 12 from FIG. 13A to FIG. 13B.

As a result of the movement of first posture sensor 15 within patient 12, posture cones 250, 252, and 254 defined based on the posture data from sensor 15 effectively change orientation and may no longer accurately indicate the posture state of patient 12. For example, as indicated by FIG. 13B, even though patient 12 occupies approximately the same posture as in FIG. 13A, the positions of posture cones 250A, 252A, and 254A are different than those of the posture cones 250, 252, and 254 shown in FIG. 13A (shown as phantom lines in FIG. 13B). In particular, the existing posture reference data (e.g., a reference coordinate vector) obtained during a prior orientation of first posture sensor 15 is no longer valid as a result of the later movement of sensor 15 relative to the body of patient 12.

Accordingly, using posture cones 250A, 252A, and 254A, which are defined based on the characteristics of first posture sensor 15 when physically oriented as indicated in FIG. 13A, to detect the posture state of a patient based on the characteristics of the posture data received from sensor 15 when physically oriented as indicated in FIG. 13B may result in processor 80 of IMD 14 incorrectly determining the actual posture states occupied by patient 12. In some examples, based on the skewed posture cones 250A, 252A, and 254A shown in FIG. 13B, processor 80 of IMD 14 may erroneously determine that patient 12 is in the undefined space between cones 250 and 252, or 250 and 254, although patient 12 is actually in the posture state represented by one of the original posture cones 250, 252, or 254. Furthermore, depending on the extent of posture sensor 15 or 17 movement, processor 80 may detect that patient 12 is in one posture state, when in fact patient 12 is in a different posture state.

Because IMD 14 is configured to deliver stimulation therapy based on the posture state detected using first posture sensor 15, the movement of posture sensor 15 within patient may result in a failure of IMD 14 to deliver efficacious stimulation therapy, e.g., by not delivering therapy or delivering therapy not suited for the actual posture state of patient 12. For example, processor 80 may control stimulation generator 84 (FIG. 4) to generate and deliver therapy to patient 12 according to a first therapy program upon detecting patient 12 is in a first posture state. However, if processor 80 incorrectly detects the first posture state because of the movement of posture sensor 15 within patient 12, and patient 12 is actually in a second posture state, the first therapy program may not provide efficacious therapy to patient 12. In some cases, however, the first therapy program may be associated with both the first and second posture states such that therapy delivery according to the first therapy program is efficacious, despite the inaccurate posture state detection by processor 80.

Referring again to both FIGS. 13A and 13B, although first posture sensor 15 has moved within patient 12 from the orientation in FIG. 13A to the orientation in FIG. 13B, the orientation of second posture sensor 17 within patient 12 has remained relatively stable. As already mentioned, one advantage to a therapy system including multiple posture sensors that are selectively used to detect posture states is that each of the posture sensors may be more effective for particular patient postures and/or activities because of their arrangement with respect to patient 12, i.e., because the implant site of the posture sensors within patient 12. In the examples shown in FIG. 13A and 13B, first posture sensor 15, which is connected to IMD 14 and positioned in the abdomen of patient 12, may be more likely to move within patient 12 than second posture sensor, which is connected to lead 16A near spinal cord 18 of patient 12. For example, the tissue in which lead 16A is implanted may be less susceptible to movement than tissue in which IMD 14 is implanted (e.g., because of the relative tissue densities), and lead 16A may also include one or more fixation elements for limiting migration of lead 16A within patient 12.

In other examples, implanting IMD 14 as a replacement for a previously implanted medical device into a larger or previously used tissue pocket, e.g., defined within tissue by the previously implanted medical device, within patient 12 may lead to rotation of the device, and thereby make first posture state sensor 15 more susceptible to disorientation. Additionally, any kind of fall experienced by patient 12 or other severe impact may move the leads or device to which one of first or second posture sensors 15, 17 is attached. Also, IMD 14 may flip or rotate in the pocket if patient 12 rubs or otherwise disturbs the device transcutaneously.

Although the description of FIGS. 13A and 13B is made with reference to examples in which first posture sensor 15 is more likely to move patient 12 than second posture sensor 17, in other examples, second posture sensor 17 may be more likely to move within patient 12 than first posture sensor 15.

Returning now to the example shown in FIGS. 13A and 13B, because second posture sensor 17 is less likely to move within patient 12 than first posture sensor 15, posture sensor 17 may be used to automatically reorient first posture sensor 15. FIG. 14 is a flowchart illustrating an example method for automatically reorienting one of first or second posture sensors 15, 17 based on posture data from the other of first or second posture sensors 15, 17. Instead of waiting for patient 12 or a clinician to initiate reorientation when it is believed that one of sensors 15, 17 has become disoriented, examples according to this disclosure include automatically reorienting a first posture sensor of a therapy system with the output from a second posture sensor of the therapy system that is implanted at a different location than the first posture sensor. For example, first posture sensor 15 may be used to automatically reorient second posture sensor 17 for one or more posture states of patient 12.

Similarly, in another example, second posture sensor 17 may be used to automatically reorient first posture sensor 15 for one or more posture states of patient 12. Although in some examples, if a posture sensor becomes disoriented for one posture state it will also be disoriented for all the other remaining patient posture states as all of the posture reference data effectively skews as shown in FIG. 13B. However, in some examples, disorientation of one posture may be independent of and therefore not affect the remaining posture states. For example, patient 12 may have an upright posture that changes over time from substantially vertical to leaning in some direction, e.g., forward or backward or to the right or left of the patient. In this example, although the upright posture of patient 12 has changed, the remaining postures, such as lying down may nevertheless remain the same.

Figure 14:
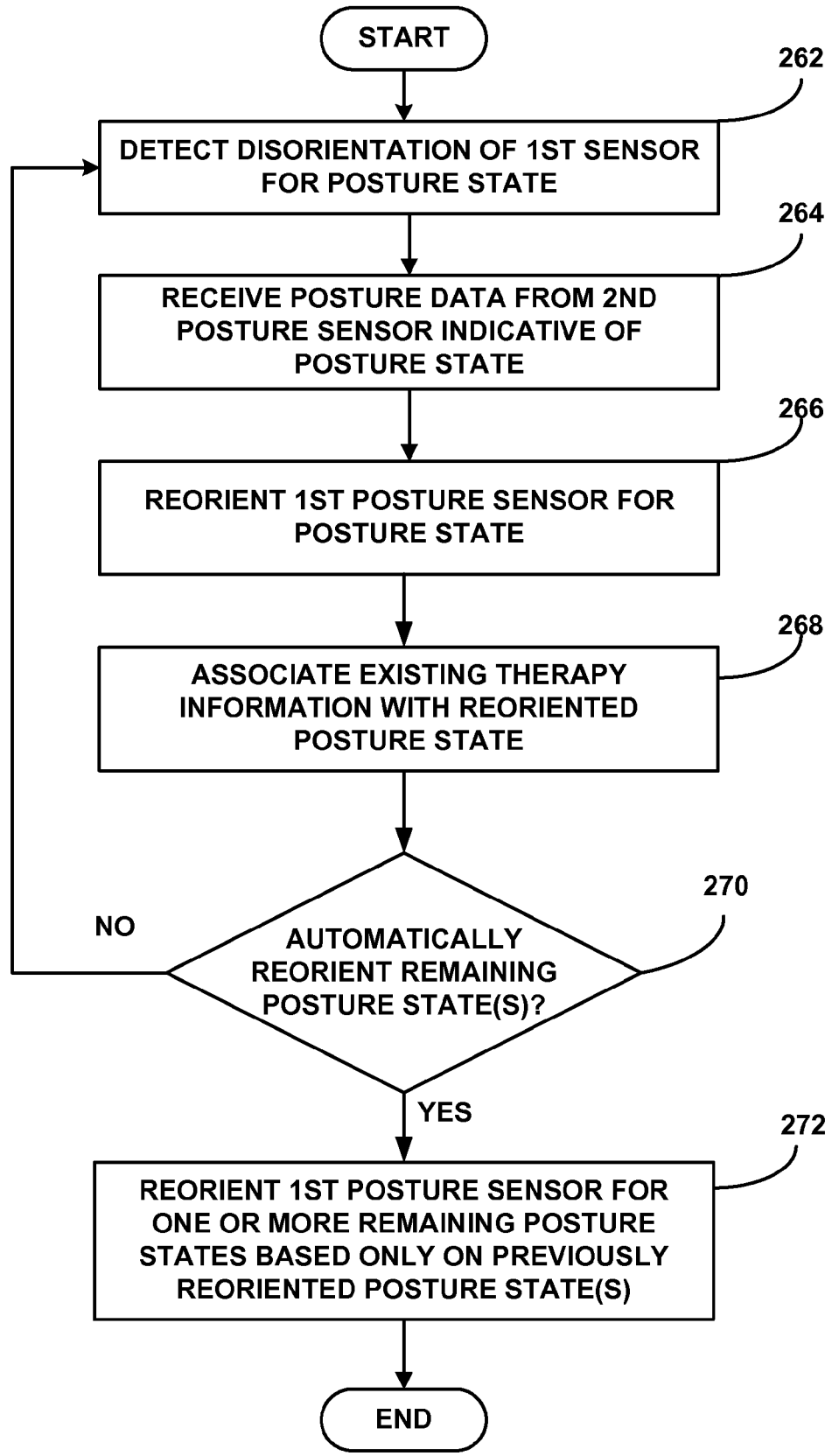
FIG. 14 is a flowchart illustrating an example technique for reorienting one posture sensor using another posture sensor.

According to the technique shown in FIG. 14, processor 80 detects disorientation of first posture sensor 15 for a first posture state of patient 12 (262). Processor 80 receives posture data from second posture sensor 17 that is indicative of a first posture state (264). First posture sensor 15 is reoriented for the first posture state (266). As described in greater detail below, reorienting first sensor 15 may include, e.g., receiving posture data from first posture sensor 15, associating the posture data from sensor 15 with a posture state determined based on posture data from second posture sensor 17, and defining posture reference data based at least in part on the posture data from first posture sensor 15 to define a reoriented posture region, e.g. posture cone corresponding to the posture state. After reorienting first posture sensor 15 (266), existing therapy information is then associated with the reoriented first posture state (268). The technique shown in FIG. 14 also includes the optional step of automatically reorienting first posture sensor 15 for one or more remaining posture states based on one or more previously reoriented posture states (272). If automatic reorientation of first posture sensor 15 for the remaining posture states is not selected, processor 80 may continue to monitor for disorientation of first posture sensor 15.

As previously described, IMD 14 modifies one or more stimulation parameters based on a determined patient posture state. Processor 80 of IMD 14 may determine the posture state of patient 12 via posture state module 86 (FIG. 4) using one or more posture state definitions, such as using the one or more posture cones or any of the other techniques described with reference to FIGS. 8A-8C. Although the example technique of FIG. 14 is described with respect to posture cones, the same or similar technique may be applied with respect to reorientation of posture sensors for posture states in general, whether the posture states are defined by posture cones or other posture regions, spatial ranges, or the like.

Posture state module 86 may include first and second posture sensors 15, 17, such as one or more single axis, two-axis or three-axis accelerometers, the signal of each of which may be processed by IMD 14 and analyzed with respect to one or more posture cones (or other posture regions) to determine (or detect) the posture state of patient 12. In some examples, first posture sensor 15 is connected to an outer housing of IMD 14 (e.g., on or within the outer housing) such that when IMD 14 moves, posture sensor 15 moves, and second posture sensor 17 may be located proximate to a therapy delivery site. For example, posture sensor 17 may be connected to medical lead 16A, which is located proximate a subcutaneous therapy delivery site within patient 12. In other examples, posture sensors 15, 17 may be positioned relative to patient 12 in other locations.

IMD 14 including first and second posture sensors 15, 17 may initially be implanted in patient 12 such that each of first and second posture sensors 15, 17 occupies a relatively stable physical orientation with respect to patient 12. Once first and second posture sensors 15, 17 and IMD 14 are implanted in patient 12, one or more posture states may be defined for patient 12 based on posture data received from each of first and second posture sensors 15, 17 when patient 12 occupies each of the physical posture states. That is, for each posture sensor 15, 17, a respective set of posture state definitions may be generated based on the output of the respective posture sensor 15, 17. For example, for each of the posture sensors 15, 17, one or more posture cones may be defined as described with reference to FIGS. 8A-8C. As described above, other posture spaces (e.g. donuts or other toroids) are contemplated in addition to posture cones. Because sensors 15, 17 are not necessarily perfectly aligned with each other within the body of patient 12, the posture data received from one sensor during the posture cone definition process for a given posture state will not necessarily be the same as posture data received from the other sensor. For instance, a vector received from sensor 15 when the patient assumes an upright posture will not necessarily be the same vector received from sensor 17 when the patient assumes this posture. Thus, in some examples, respective sets of posture reference data must be collected for each of posture sensors 15 and 17 during the process of defining posture cones for various postures states of patient 12.

In some examples, for each of posture sensors 15 and 17, a posture state cone may be defined based on posture reference data, which may comprise a posture vector (e.g., a reference coordinate vector) derived from the posture data obtained from the posture sensor at a time when patient 12 is in a known posture state. In some examples, a posture cone is defined by a reference coordinate vector generated by a particular posture sensor 15, 17 for a given posture state in combination with a distance or angle defining a range of coordinate vectors within a cone surrounding the posture reference coordinate vector. The reference coordinate vector may be, for example, a vector determined based on the output of the respective posture sensor 15, 17 when patient 12 is in a known posture state. In other examples, a posture cone is defined by a reference coordinate vector and a range of cosine values computed using the reference coordinate vector as an adjacent vector and any of the outermost vectors of the cone as a hypotenuse vector. The use of cosine values, in some cases, may provide substantial processing efficiencies.

Once a posture state is defined, IMD 14 may selectively receive posture data from one of first or second posture sensors 15, 17 and determine a posture vector based on the posture data. If the determined vector is within the maximum distance from the posture vector of the posture cone defined by the posture reference data that corresponds with the sensor from which the data was received, e.g., as determined by the tolerance, processor 80 of IMD 14 determines that patient 12 is in the posture state associated with the posture cone. For example, in some examples, a posture cone may be defined by a reference coordinate vector for a given posture state in combination with a distance or angle defining a range of coordinate vectors within a cone surrounding the posture reference coordinate vector. Thus, if the sensed posture vector indicative of the current patient posture state is within the defined angle or distance of the reference coordinate vector, the posture state vector is determined to reside within the posture cone defined by the reference coordinate vector, and processor 80 determines that patient 12 is in the posture state associated with the cone In other examples, a posture cone may be defined by a reference coordinate vector and a range of cosine values computed using the reference coordinate vector as an adjacent vector and any of the outermost vectors of the cone as a hypotenuse vector. If the determined vector generated by the posture state sensor and the reference coordinate vector produce a cosine value in a specified cosine range, then posture state vector is determined to reside within the posture cone defined by the reference coordinate vector, and processor 80 determines that patient 12 is in the posture state associated with the cone.

Such a process for determining a patient posture state based on an output from a posture sensor may be repeated to define multiple posture cones defining multiple posture states, e.g., posture states that may be useful with respect to the delivery of electrical stimulation therapy.

In this manner, one or more posture state cones may be defined for each of sensors 15, 17 such that processor 80 of IMD 14 may detect when patient 12 occupies a posture state defined by one of the posture cones based on posture data received from one of first or second posture sensors 15, 17. As previously described, in some examples, IMD 14 selects (or modifies) one or more stimulation therapy parameter values based on the determined patient posture state. For example, based on the posture state of patient 12 detected by IMD 14, IMD 14 may deliver therapy according to one or more stimulation programs that are defined to provide effective therapy to patient 12 when patient occupies the posture state detected by IMD 14. When IMD 14 determines that patient 12 changes posture states based on data from one of first or second posture sensors 15, 17 and the posture cones defined by the posture reference data for the sensor, processor 80 may modify one or more therapy parameter values, of the stimulation therapy, such as current or voltage amplitude, according to the program that is associated with the new posture state occupied by patient 12.

In order to deliver posture-responsive therapy, memory 82 of IMD 14 may associate therapy information with each of the respective sets of posture reference data for one or more of the defined posture cones for one or more of first and second posture sensors 15, 17. For example, memory 82 may store a look-up table or other data structure for each of first and second sensors 15 and 17. Each such data structure may contain records, in which each record contains therapy information associated with a defined posture state. These programs may define stimulation parameter values that provide effective stimulation therapy to patient 12 when patient 12 is in the respective posture state indicated by the posture state signature.

Therapy information may include any of a variety of information useful in controlling posture-responsive therapy, analyzing posture-responsive therapy, analyzing patient posture state activity, patient therapy adjustments, or the like. For example, therapy information may include information indicating a history of patient posture state activity over a period of time, such as statistics relating to numbers of time posture states are assumed, numbers of particular posture state transitions from one posture state to another, time spent in different posture states, times of the day associated with different posture states, and related statistical information such as average, mean and trend information.

Therapy information also may include therapy parameter values that define efficacious therapy for each posture state. Examples of therapy parameter values include voltage or current amplitude, pulse width, pulse rate, electrode configurations, program groups and programs used for particular posture states. In addition, therapy information may include information indicating a history of patient therapy adjustments in different posture states, including increases, decreases and other adjustments, and related statistical information such as average, mean and trend information. In some respects, this type of information may generally be referred to as parameter information in the sense that it may be used to identify and program efficacious parameters for different posture states. Therapy information may be useful in programming the IMD 14. Therapy information also may be useful in evaluating therapeutic efficacy, patient activity levels, patient quality of life, or other therapy-related metrics. In some cases, parameter information may be collected and stored by IMD 14 as part of a "record" mode. Hence, in some implementations, IMD 14 may have record and posture-responsive therapy modes, where the record mode may be useful in programming parameters for use in the posture-responsive therapy mode.

When initially defining a posture cone, IMD 14 may store the posture cone definition information as an entry in a look-up table or other data structure that is associated with the one of first or second sensors 15, 17 for which the posture cone is being defined. As previously indicated, in some examples, each sensor 15, 17 may be associated with respective sets of posture state definitions that are based on the reference coordinate vectors generated for the respective posture sensor 15, 17. Thus, in some examples, IMD 14 stores respective data structures for each of the posture sensors 15, 17 of therapy system 10. One or more stimulation programs that may provide effective stimulation therapy to patient 12 when occupying the posture state may be stored in the tables to correspond to the defined posture cones. The tables associated with the posture state sensors 15, 17 may have the same stimulation program information for similar posture states.

When IMD 14 receives posture data from one of first or second posture sensors 15, 17, processor 80 of IMD 14 compares the data to all of the defined posture cones stored in the associated look-up table until a match is found. If the posture data from one of posture sensors 15, 17 falls within a posture cone defined by the associated posture reference data, processor 80 controls stimulation generator 84 (FIG. 4) to generate and deliver stimulation according to the stimulation program(s) corresponding to the posture cone in the associated look-up table. Additionally, any modifications to the programs may also be stored in such a look-up table.

In some examples, the therapy information associated with a defined posture cone may include modifications to the definition of the posture cone itself. Posture cone modifications may include adjustments to the tolerance value used in conjunction with a posture vector, as described above. While the initial tolerance value may be predefined value, such as an angle, it may be observed that the resulting posture cone may define a posture state region (e.g., a posture cone) that is too small or too great based on the therapy experienced by a patient over time. Accordingly, a new tolerance value may be defined for a posture cone. This tolerance value adjustment may also be stored as an entry in a look-up table such that the value adjustment is associated with the respective posture cone definition it is modifying.

Therapy information may be valuable to the patient and/or clinician provided that it is properly associated with posture reference data that accurately defines the posture states. When the accuracy of previously obtained posture reference data is compromised due to disorientation of one of first or second posture sensors 15, 17, the therapy information associated with the posture reference data is less useful. However, acquisition of the therapy information may be a labor and time-intensive effort. In some cases, the therapy information may have been obtained over the course of several days, weeks or months, and required substantial time and effort by the patient and/or clinician. Therefore, reacquisition or resetting of the therapy information is generally undesirable.

In accordance with various aspects of this disclosure, therapy information may be retained and associated with posture state reference data that is newly defined (e.g., updated) as a result of a reorientation procedure. The therapy information is still relevant for the actual posture states of the patient. When disorientation of one of posture sensors 15, 17 occurs, however, the previously obtained posture reference data for the disoriented posture sensor may no longer accurately define the posture states. Upon reorientation of the posture sensors 15, 17, e.g., using the technique shown in FIG. 14, the newly defined posture reference data for the disoriented posture sensor may more accurately define the posture states. Therefore, the previously obtained therapy information may be associated with the newly defined posture reference data for the appropriate posture states, rather than discarded.

As an illustration, it is assumed that the therapy information includes, among other things, amplitude values that result in efficacious stimulation therapy when the patient occupies different posture states. In some cases, the stimulation amplitudes are selected and defined based on data obtained during the use of a fundamental recording mode in which manual patient adjustments are monitored over a period of time to obtain an indication of efficacious amplitude values useful in different posture states, further manual adjustments made by patient 12 following activation of posture-responsive therapy, and in-clinic evaluation of patient 12 by the clinician.

It may be undesirable to simply discard such amplitude values. Rather, because the amplitude values relate to posture states, and posture states reside at a level of abstraction above the actual posture reference data used to define the posture states, the amplitude values may simply be associated with posture reference data that is newly defined for the pertinent postures as a result of a reorientation process shown in FIG. 14. In this manner, the relationship between the amplitude values and the posture states to which they pertain may remain intact following reorientation.

As previously described, at some point in time, including a point in time after posture state definitions (e.g., posture cones) for each of the first and second posture sensors 15, 17 have been defined for one or more posture states and therapy information has been associated with one or more of the posture state definitions, one of sensors 15, 17 implanted in patient 12 may become disoriented, e.g., as a result of a physical movement of one of the sensors within patient 12. As a result, the ability of IMD 14 to accurately detect the posture state actually occupied by patient 12 using the defined posture state definitions may become impaired, as illustrated, e.g., by FIGS. 13A and 13B.

Referring again to FIG. 14, in some examples, IMD 14 is configured to monitor the status of first and second posture sensors 15, 17 to detect if one of sensors 15, 17 has become disoriented for a posture state of patient 12 (262). In some examples, IMD 14 utilizes patient posture state behavior over a period of time, e.g., daily, weekly, etc., to determine if it is likely that one of first or second posture sensors 15, 17 has been disoriented. For example, IMD 14 may recognize typical periods of time during which patient 12 is sleeping and, thus, should be occupying one or more lying down posture states. If processor 80 of IMD 14 determines that the posture state of patient 12 detected by one of first or second posture sensors 15, 17 at those times is not a lying posture state, processor 80 may take suitable action, such as initiating an automatic reorientation procedure for the disoriented sensor in accordance with examples disclosed herein.

In other examples, IMD 14 monitors patient posture state to determine one or more patterns of patient behavior or activity over time. If processor 80 of IMD 14 detects a posture state or a series of posture states that are not consistent with the determined pattern, processor 80 may take an appropriate action, such as reorienting the posture sensor 15, 17 that is determined to have changed orientation (266). The disoriented posture sensor is referred to as the "first sensor" in FIG. 14. As another example, IMD 14 may be configured to monitor for sensor disorientation using input from patient 12. Patient 12 periodically communicate with IMD 14 to identify a posture state currently being occupied by patient 12 or about to be occupied by patient 12. Processor 80 of IMD 14 may verify that the posture state detected using one of first or second posture sensors 15, 17 is consistent with the state indicated by patient 12. If the patient-indicated posture state does not match the posture state indicated by one of first or second posture sensors 15, 17, processor 80 may determine that the one of first or second posture sensors 15, 17 has changed orientation since the posture state definitions for the posture sensor were determined.

All of these examples of detecting the disorientation of one of first or second posture sensors 15, 17 for a posture state of patient 12 may be used in conjunction with or replaced by comparing posture data received from one of first or second posture sensors 15, 17 to posture data received from the other of first or second posture sensors 15, 17. In such cases, IMD 14 may determine if first and second posture sensors 15, 17 are providing inconsistent posture data, which may in turn indicate the disorientation of one of the sensors. In some examples in which a direct comparison between the posture data received from sensors 15 and 17 is used, the relationship between the posture reference data for each sensor (e.g., the posture state definitions) when both of the sensors were both oriented properly may need to be known. For instance, vectors may be obtained from both of first and second sensors 15, 17 when patient 12 is upright. As discussed above, the vectors for each of sensors 15, 17 need not be in alignment because the sensors are not necessarily oriented the same within the body of patient 12. However, a known spatial relationship may be known between the vector of first sensor 15 and the vector of second sensor 17. When this spatial relationship changes, it may be ascertained that one of first or second posture sensors 15, 17 has become disorientated. Comparing posture data from first and second posture sensors 15, 17 may be performed by processor 80 of IMD 14 on a substantially continuous basis, or may be implemented periodically based on other indicators including, e.g., when one of the other techniques described above indicates a potential problem with one of first or second posture sensors 15, 17.

In addition to detecting disorientation of first posture sensor 15 (262), processor 80 receives posture data from second posture sensor 17 that indicates patient 12 is in the first posture state (264). Instead of interrupting therapy delivery to patient 12 by IMD 14 and waiting for patient 12 or a clinician to indicate, e.g. via external programmer 20 the actual posture state that patient 12 is occupying when processor 80 detects first posture sensor 15 is not properly oriented, processor 80 automatically reorients sensor 15 based on posture data received from another sensor 17. In this way, a therapy system including multiple posture sensors that independently indicate a patient posture state may be useful for reorienting and recalibrating one or more of the posture sensors based on the output of another posture sensor.

When processor 80 detects that first posture sensor 15 is disoriented (262), processor 80 may interrogate second posture sensor 17 for posture data that indicates the actual posture state of patient 12 (264). As previously described, posture states of patient 12 may be represented by posture cones that are defined based on one or more characteristics of the posture data (e.g., reference coordinate vectors) received from one of posture sensors 15, 17, which form posture reference data, while patient 12 occupies different posture states. Using the posture cones such as cones 250, 252, and 254 shown in FIGS. 13A and 13B, IMD 14 may detect the posture state of patient 12 by comparing the posture data received from second posture sensor 17 to the space defined by each posture cone 250, 252, and 254 as defined by the posture reference data for second posture sensor 17.

Once processor 80 determines the actual posture state of patient 12 based on the output of second posture sensor 17, first posture sensor 15 may be reoriented for at least that posture state, which is referred to as the first posture state for ease of description of the reorientation technique (266). In some examples, the clinician or another person has determined that posture sensor 17 is the relatively more stable posture sensor, and, therefore, can be used to indicate disorientation of the other posture sensor 15 and/or reorient sensor 15. Reorienting a posture sensor may involve substantially the same process used to initially orient the sensor for a posture state. In general, reorienting first posture sensor 15 may include receiving posture data from first posture sensor 15 and defining posture reference data based at least in part on the data received from first posture sensor 15 to define a reoriented posture region for sensor 15 corresponding to the first posture state.

In some examples, similar to the posture cone definition process previously described, a posture vector (e.g., a reference coordinate vector) may again be defined based on the posture data received from the now disoriented first posture sensor 15, and a tolerance value (e.g. angle, cosine value, or range of cosine values) may be used to define a new posture cone for the first posture state. In some examples, IMD 14 redefines the posture cone for the disoriented first posture sensor 15 by shifting the previously defined posture cone in space by a magnitude that is based on a comparison between the posture vector from posture sensor 15 before it became disoriented and a posture vector derived from posture data received from the now disoriented sensor 15.

For example, processor 80 may determine that at a current time, second posture sensor 17 indicates patient 12 is the first posture state. Processor 80 may determine the current vector generated by the output from posture sensor 15 (e.g., if sensor 15 includes a three-axis accelerometer) at that time, and characterize the current vector as the new reference coordinate vector for the first posture state definition that is associated with first sensor 15. By comparing the orientation of the current vector to the orientation of a previously defined reference coordinate vector that is a part of the stored first posture state definition for first sensor 15 (e.g., determined prior to disorientation of sensor 15), processor 80 may determine the angle or other tolerance by which the reference coordinate vector has shifted since the previous definition for the first posture state was generated. Thus, processor 80 may shift the previously defined posture state definition by that angle or other tolerance in order to reorient sensor 15 for at least the first posture state and, in some examples, maintain a substantially similar posture cone (or other posture state region).

In subsequent posture state detections, processor 80 references the redefined posture cone (or other posture state definition) to detect the posture state of patient 12, e.g., by comparing the posture reference data for the redefined cone to posture data received from first posture sensor 15. In this manner, IMD 14 may determine the posture state actually occupied by patient 12 even after first posture sensor 15 has become disoriented as a result of, e.g., sensor 15 changing physical orientation with respect to patient 12.

The above examples of reorienting first posture sensor 15 assume that patient 12 is in an ideal posture state, e.g., patient 12 is occupying a posture in which a sense vector from the stable sensor 17 is at or within a predetermined tolerance (e.g., within one degree or within a particular cosine value range) of the reference coordinate vector used to define the posture state. For example, the ideal posture state may occur when patient 12 is standing straight up not leaning forward, backward, or to the right or the left, such that a sense vector determined based on output from sensor 17 is within a predetermined tolerance of the reference coordinate vector used to define the upright posture state.

Thus, in some examples, processor 80 may only reorient first posture sensor 15 for the first posture state using the technique described above when it is known that patient 12 occupies a near ideal version of that posture state, e.g., when patient 12 is standing approximately straight up. In some such examples, after it is determined that first posture sensor 15 is disoriented for a posture state (or multiple posture states) of patient 12, IMD 14 may selectively determine the posture of patient 12 based on posture data received from only second posture sensor 17 for a period of time until the ideal posture state is detected based on second posture sensor 17. In this manner, IMD 14 may essentially render first posture sensor 15 dormant until an accurate reorientation may be carried out for the sensor.

While selectively determining posture based only on posture data received from sensor 17, processor 80 may periodically or continuously analyze the posture data received from the second posture sensor 17 that corresponds to the disoriented posture state of first sensor 15 to determine when patient 12 occupies a near ideal version of the disoriented posture state. For example, processor 80 may analyze the posture data received from the second posture sensor 17 to determine when the posture vector derived from the received data is close to the reference vector that defines the posture cone for which first sensor 15 has become disoriented. When it is determined from the posture data received from second posture sensor 17 that patient 12 is within a threshold range (e.g., as indicated by an angle, distance or cosine value) of an ideal posture state (e.g., standing straight up or lying down with little to no inclination), processor 80 may proceed to reorient first posture sensor 15 by simply defining a reoriented posture state cone based on new posture reference data that includes, e.g., a posture vector derived from posture data received from the disoriented first sensor 15. In some examples, the ideal posture state threshold range may correspond to posture data that produces a posture vector offset from the reference vector for that posture state by an angle between and including approximately 1 and 5 degrees.

However, in many cases, when one of first or second posture sensors becomes disoriented, patient 12 may be in some non-ideal posture state. For example, patient 12 may be leaning forward, in which case posture data received from a posture sensor may produce a vector that is within the posture cone associated with the upright posture but that does not correspond exactly to the reference vector that defines the upright cone. In such cases, the posture data received from the disoriented sensor may not represent an ideal posture state and therefore it may not be appropriate for deriving posture reference data to construct a new posture cone at that time. In such circumstances, other techniques may need to be employed to reorient the disoriented posture sensor.

In some examples in which patient 12 is not in an ideal or near ideal posture state when first posture sensor 15 becomes disoriented for that posture state, the disoriented sensor may be reoriented based on a derived relationship between the posture data received from second sensor 17 and the posture reference data for sensor 17 corresponding to the posture state for which sensor 15 has become disoriented. This reorientation technique may also be used even if patient 12 is in an ideal posture state. According to this reorientation technique, first sensor 15 may be reoriented for the first posture state based on a relationship between the vector determined from posture data received from second sensor 17 when patient 12 occupies the first posture state and the stored reference coordinate vector for the definition of the first posture state associated with second sensor 17.

In some examples, after determining sensor 15 has become disoriented for at least the first posture state, processor 80 of IMD 14 (or a processor of another device) determines a difference vector by subtracting the stored reference coordinate vector for the first posture state definition associated with the stable sensor 17 from the sense vector that is determined based on posture data from sensor 17 at the time the first posture state is detected. As described with respect to FIGS. 8A-8C, the reference coordinate vector may define, at least in part, a posture cone or other posture state definition.

The difference vector may be used to derive a new reference coordinate vector to redefine the definition for the first posture state associated with the disoriented first sensor 15. In particular, processor 80 may add the difference vector to a sense vector determined based on the posture data received from the disoriented first posture sensor 15 at the time the first posture state is detected based on the stable sensor 17 to yield a properly oriented reference coordinate vector from which the posture state definition for the first posture state may be determined for sensor 15. In some examples, the same tolerance that was previously used to define the definition of the first posture state for first sensor 15 may be applied to the derived reference coordinate vector for first sensor 15 to update the definition for the first posture state for the reoriented sensor 15.

The difference vector may indicate the relative orientation between the currently detected first posture state and the "ideal" posture state, as indicated by the reference coordinate vector associated with the first posture state definition for the stable sensor 17. In this way, the difference vector can indicate the relative location of the first posture state within the posture region defining the first posture state for second sensor 17. In examples in which the first and second sensors 15, 17 are associated with similar posture state regions (which may have different orientations relative to each other but similar tolerance values relative to a reference coordinate value), the relative location within the posture region defining the first posture state for second sensor 17 corresponds to the location at which the first posture state lies within the posture region defining the first posture state for first sensor 15. Thus, by knowing how the vector that is determined based on the posture state data from first sensor 15 relates to the posture state region for the first posture state, processor 80 may determine the relative orientation of a reference coordinate vector for the definition of the first posture state that is based on the current position of first sensor 15. The current position of first sensor 15 may be determined based on the sense vector determined based on the output of first sensor 15 at the time processor 80 detects the first posture state based on second sensor 15. The relative location between the reference coordinate vector and sensed vector for the stable sensor 17 may be applied to the sensed vector for first sensor 15 to determine the reference coordinate vector for the first posture state definition for first sensor 15. In this way, the first posture state definition associated with first sensor 15 may be reoriented based on data from second sensor 17. As previously described, in some examples, existing therapy information that was previously obtained based on the initial orientation may be associated with the redefined posture reference data (268), thereby maintaining the relationship between the therapy information and the actual posture states occupied by the patient. The therapy information may be associated with the redefined posture reference data in memory 82 (FIG. 4) of IMD 14 and/or memory 108 (FIG. 6) of an external programmer 20, so that the therapy information may be used in the posture-responsive therapy, e.g., to select appropriate stimulation parameter values for different posture states, and/or in other operations such as analysis and review of posture state activity, posture state transitions, patient therapy adjustments, or the like.

Again, rather than erase the therapy information associated with a posture cone for one of first or second posture sensors 15, 17 that has been redefined, in some examples, IMD 14 automatically associates the therapy information with the new posture cone (defined by the redefined posture reference data) that is replacing the old posture cone (defined by the previously defined posture reference data) for the sensor that had become disoriented. In this manner, the process of associating the therapy information with the new posture cone does not have to be repeated as when the initial posture cone was defined. Further, any therapy modifications that have been made to one or more stimulation programs associated with an old posture cone may automatically be associated with the new posture cone defining the same or similar posture state of patient 12.

For example, IMD 14 may store the new posture cone information as a new entry in a look-up table or other data structure that is associated with the sensor that had become disoriented and subsequently reoriented, or replace part of a look-up table mapping with the newly defined posture reference data that defines the new posture cone. Although, in some examples, the old posture cone information is erased and replaced by the new posture cone definition information (i.e., the redefined posture reference data), in other examples, the new posture cone definition information may be entered without erasing the old posture cone definition information. Instead, processor 80 of IMD 14 may "deactivate" the old posture cone definition and "activate" the redefined posture reference data defining the new, reoriented posture cones. Subsequently, when processor 80 of IMD 14 is determining whether or not posture data from one of first or second posture sensors 15, 17 corresponds to a posture cone definition stored in the look-up table, it may only compare the signal to the active posture reference data for each respective posture state. However, all of the therapy information that was associated with the now inactive posture reference data for the previous posture cones may be automatically associated with the newly active posture reference data for the newly reoriented posture cones in the look-up table.

As previously mentioned, therapy information associated with a defined posture cone may include modifications to the definition of the posture cone itself. In some examples, these modifications may be automatically associated with the redefined posture cone for the respective posture state. For example, the modification, e.g., an adjusted tolerance value, may be automatically applied to the posture cone definition information stored in a look-up table. It may be desirable, in some examples, to apply the cone definition modification to the relevant posture cones for both first and second sensors 15, 17 so that posture state definitions will remain consistent between both sensors. In this manner, therapy information used to tailor posture cone definitions may be automatically applied to the new posture cone without requiring patient intervention, with or without the assistance of a clinician.

In some cases, the therapy information may not be automatically associated with posture reference data for a redefined posture cone, but instead patient 12 or a clinician may be given the option of associating parts or all of the therapy information from the old posture cone to the new posture cone, e.g., via programmer 30 or programmer 60. The ability to selectively associate all or part of the previously obtained therapy information with the redefined posture reference data may provide patient 12 or a clinician with added flexibility, particularly in the event that the clinician would like to reacquire new therapy information for all or selected items of therapy information upon reorientation.

Furthermore, in some examples, the posture state identified by IMD 14 may be objectified to evaluate one on more aspects that may be based on the posture state of a patient, as mentioned above. By importing the modification made to a previous posture cone, a redefined posture cone may define a posture space that is effectively the same as the posture cone defined for the posture state prior to the disorientation of one of first or second posture sensors 15, 17. Accordingly, for the purposes of objectifying the posture state of a patient, information gathered using a previous cone should correspond to the information gathered using the redefined cone such that there should be no requirement to distinguish between the two types of information for purposes of objectification, or evaluation of posture state information in general.

In some examples, more than one posture cone is defined for patient 12. For example, IMD 14 may store one posture cone that defines an upright posture state to detect when patient 12 is in an upright posture state, another posture cone that defines a lying right posture state to detect when patient 12 is lying on a right side of the body, another posture cone that defines a lying left posture state when patient 12 is on a left side of the body, and so forth. Depending on the disorientation of one of first or second posture sensors 15, 17, it may be necessary to redefine each of the posture cones for each of the respective postures. Hence, the general process outlined in FIG. 14 may be applied to redefine multiple cones. In addition, the process of FIG. 14 may be applied, in some instances, to repeat reorientation multiple times, in the event disorientation is detected multiple times.

Several techniques may be used to redefine multiple posture cones corresponding to multiple patient posture states. For example, individual posture cones may be sequentially redefined by IMD 14 as the device detects one of first or second posture sensors 15, 17 has become disoriented for multiple posture states of patient 12. In some examples, each posture cone for one of first or second posture sensors 15, 17 may stay active up to the time that all posture cones have been redefined for the posture sensor. By permitting some posture cones to be defined based on posture data from one of first or second posture sensors 15, 17 in the "old" orientation at the same time as the posture cones based on posture data in the current orientation, until all of the posture cones have been redefined, two or more posture cones may overlap for a period. Accordingly, in some cases, IMD 14 may suspend the use of all posture cones to detect patient posture states until each of the posture cones is redefined. However, in some cases, IMD 14 may also continue therapy with respect to the posture cones that have not been redefined and simply reorient one of first or second posture sensors 15, 17 for other posture states as IMD 14 detects the need, i.e. as IMD 14 detects disorientation of one of sensors 15, 17 for another posture state.

As multiple versions of posture cones for any one posture state may exist in parallel, in some examples, memory 82 of IMD 14 may store hierarchal instructions for determining a posture state of patient 12 when posture data from one of first or second posture sensors 15, 17 indicates a coordinate vector that is located in a space of more than one posture cone. For example, in some cases, processor 80 may detect the posture state corresponding to the most recently defined posture cone, thereby acting under the assumption that the most recently defined posture cone is the most accurate with respect to the actual posture state of patient 12. Using such hierarchal instructions, IMD 14 may be allowed to detect a patient posture state even if one or more posture cones overlap, e.g., for the reasons previously described.

In other examples, IMD 14 may automatically reduce the tolerance value of one or more of the overlapping cones such that they no longer overlap. For example, the tolerance value of a posture cone based on the orientation one of sensors 15, 17 may automatically be reduced until the cones in question no longer overlap. In this manner, by changing the posture reference data for "old" posture cone and not changing the tolerance value of the posture reference data for "new" posture cone, once all of the posture cones have been redefined based on the current sensor orientation, these posture cones should more accurately define the posture states of patient 12 as compared to a technique in which the tolerance value of a "new" posture cone may be adjusted. However, in some examples, the tolerance value of the "new" posture cone may also be adjusted such that respective cones do not overlap.

In addition to or instead of sequentially reorienting first posture sensor 15 as IMD 14 detects sensor disorientation for multiple posture states, IMD 14 may automatically reorient sensor 15 for one or more of the remaining posture states based on one or more previously reoriented posture states (272). For example, IMD 14 may establish a relative relationship between one or more posture states such that a plurality of the posture states may be redefined by simply redefining one or more reference cones. In one such example, if posture cone A has a known geometric relationship to posture cones X, Y and Z, then it may be possible to redefined the posture reference data for posture cone A based on the redefined posture reference data for posture cones X, Y and Z. In this case, the patient may occupy pertinent posture states for posture cones X, Y and Z but does not need to occupy the posture state for posture cone A. In this manner, IMD 14 may redefine one or more posture cones without requiring patient 12 to actually occupy the posture state corresponding to the posture cone when the posture cones are redefined (e.g., reoriented based on a posture vector).

As discussed above, based on the originally defined posture cones or some posture cones defined thereafter, IMD 14 may establish the relative position of posture cones with respect to one or more reference cones. For example, for posture cones defined in two-dimensional space, the approximate angle of a posture vector of a posture cone with respect to a posture vector of a reference posture cone may be periodically determined and stored by IMD 14. Using this known relationship, in addition to established tolerance values, IMD 14 may automatically redefine posture cones once the reference posture cone is redefined. Using the posture cones 142, 144, 146, and 148 of FIG. 8A as an example, all of the cones lie in the same plane and each of the cones posture vectors are offset from one another by 90°. Because of this known geometric relationship between cones 142, 144, 146, and 148, the posture reference data for any of the cones can by redefined based on a single reoriented cone. For example, if cone 142 is reoriented based on posture reference data that defines a cone with a posture vector offset from axis 141 by 30° in the same plane as shown in FIG. 8A, the remaining cones 144, 146, and 148 can be automatically redefined by shifting their respective posture vectors by 30° in the same direction as cone 142 has shifted. In some cases, a similar technique may be used for posture cones defined in three-dimensional space, e.g., using two or more reference cones. Again, although posture cones are described for purposes of illustration, other posture regions such as cylinders or the like may be used.

In some examples, rather than determining the angular relationship between a posture vector and reference cones, IMD 14 may analyze the relative spatial difference between the space defined by a redefined posture cone and the space defined by the posture cone it is replacing. For example, using a relative coordinate system, a translation value may be established in each axial direction by analyzing the difference between one or more reference points common to the redefined posture cone and the previous cone. For example, it may be determined that the space of a redefined posture cone has only effectively moved 2 units in one axial direction based on a comparison of the redefined posture cone to the posture cone it is replacing. In such an example, IMD 14 may automatically translate the remaining posture cones such that they are redefined consistent with the movement of two units in the same axial direction.

Posture reference data, defining posture cones or other posture regions, are not limited to being redefined one time but instead may be redefined multiple times. For example, a posture cone that redefined an original posture cone may be further replaced by another redefined cone. In such examples, IMD 14 may associate some or all of the therapy information corresponding to the first redefined cone to the second redefined cone, in addition to therapy information associated with the original posture cone, which may or may not be associated with the first redefined cone. Such a function may be accomplished using the data structures previously described, e.g., a look-up table.

This disclosure provides multiple features to users of implantable therapy systems. Employing multiple posture sensors in a single therapy system may accommodate a variety of conditions encountered by patients in varying posture states over a period of time, the accommodation of which may improve therapy efficacy and increase the reliability and longevity of posture-responsive features. In one example, the multiple posture sensors may be selectively activated based on the effectiveness of a sensor in sensing a particular patient posture and/or activity level. Associating different posture sensors arranged in different locations with different posture states may improve the delivery of posture-responsive therapy by providing a sensor particularly suited for each particular posture among the plurality of postures of the patient.

In another example, the multiple posture sensors may be selectively activated based on one of the sensors malfunctioning or failing, losing a posture state orientation, or measuring a posture state inaccurately. In such cases, examples according to this disclosure improve the reliability and longevity of posture-responsive therapy systems by providing a redundant posture sensor system that automatically (or through user intervention) toggles to one posture sensor based on the sensed status of the other sensors in the system. In this way, the therapy system includes at least one back-up posture sensor in the event that another posture sensor of the therapy system is unavailable to provide posture state information.

In addition to selectively receiving posture state input from only one of multiple posture sensors at any given time or selectively determining a posture state based on data from only one of the multiple posture sensors at a time, one of the posture sensors may also be employed by IMD 14 to automatically reorient another sensor for one or more posture states in the case of sensor disorientation. Automatically reorienting one posture sensor based on input from another posture sensor has several advantages over, e.g., manually reorienting sensors by requiring a patient to occupy a posture state and manually commanding the IMD to reorient the sensor. Automatic reorientation may enable implantable medical systems according to this disclosure to seamlessly deliver uninterrupted therapy to a patient in spite of posture sensor disorientation. There is no need to interrupt therapy to reorient the posture sensor, e.g., with clinician intervention, and therefore patient 12 may continue to receive posture responsive therapy. Additionally, the patient can, in some cases, save a trip to see a clinician to reprogram the IMD. In general, the reorientation process may be completely transparent to the patient, which in turn may make treatment and operation of the device less complex and time consuming for the patient.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to cause one or more processors to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that my benefit from the subject matter of this disclosure.

Many examples have been described. Various modifications may be made without departing from the scope of the invention as defined by the claims that follow. These and other embodiments are within the scope of the following claims.

The invention claimed is:

1. A method comprising:
 detecting, by a processor of a therapy system, a change in orientation of a first posture sensor of the therapy system, wherein the therapy system provides posture responsive therapy to a patient; and
 automatically reorienting, by the processor, the first posture sensor based on posture data from a second posture sensor of the therapy system.

2. The method of claim 1, wherein reorienting the first posture sensor comprises:
 receiving posture data from the first posture sensor;
 associating the posture data from the first posture sensor with a posture state determined based on the posture data from the second posture sensor; and
 defining a reoriented posture region corresponding to the posture state with posture reference data based at least in part on the posture data from the first posture sensor.

3. The method of claim 2, wherein the posture region comprises a posture cone, and wherein the posture reference data comprises one of:
 a posture coordinate vector and a tolerance angle that define the posture cone, or
 a posture coordinate vector and a range of cosine values corresponding to an angle between the posture coordinate vector and a boundary vector of the posture cone.

4. The method of claim 2, wherein the posture region comprises at least one of a posture cone or a posture toroid.

5. The method of claim 1, further comprising:
 determining therapy information associated with a first posture state definition that is based on first posture data from the first posture sensor before reorienting the first posture sensor; and
 associating the therapy information with a second posture state definition that is based on second posture data from the first posture sensor after reorienting the first posture sensor.

6. The method of claim 1, wherein reorienting the first posture sensor comprises reorienting the first posture sensor for a plurality of posture states based on the posture data from the second posture sensor.

7. The method of claim 1, wherein reorienting the first posture sensor comprises:
    determining a first sense posture vector based on posture data received from the second posture sensor;
    comparing the first sense posture vector to a posture region associated with the second posture sensor to determine a posture state of the patient, wherein the posture region is defined by posture reference data comprising a first reference coordinate vector;
    subtracting the first reference coordinate vector from the first sense posture vector to determine a difference vector;
    determining a second sense posture vector based on posture data received from the first posture sensor while the patient occupies the posture state;
    adding the difference vector to the second sense posture vector to determine a second reference coordinate vector for the first posture sensor; and
    defining a reoriented posture region for the first posture sensor corresponding to the posture state of the patient with posture reference data based at least in part on the second reference coordinate vector.

8. An implantable medical system comprising:
    a first posture sensor that generates posture data indicative of a posture state of a patient;
    a second posture sensor that generates posture data indicative of a posture state of the patient; and
    a processor that detects a change in orientation of the first posture sensor, receives posture data from the second posture sensor, and reorients the first posture sensor based on the posture data from the second posture sensor.

9. The system of claim 8, wherein the processor reorients the first posture sensor by at least associating the posture data from the first posture sensor with a first posture state determined based on the posture data from the second posture sensor, and defining a reoriented posture region corresponding to the first posture state with posture reference data based at least in part on the posture data from first posture sensor.

10. The system of claim 9, wherein the posture region comprises a posture cone, and wherein the posture reference data comprises one of:
    a posture coordinate vector and a tolerance angle that define the posture cone, or
    a posture coordinate vector and a range of cosine values corresponding to an angle between the posture coordinate vector and a boundary vector of the posture cone.

11. The system of claim 9, wherein the posture region comprises a posture toroid.

12. The system of claim 8, wherein the processor determines therapy information associated with a first posture state definition that is based on first posture data from the first posture sensor before reorienting the first posture sensor and associates the therapy information with a second posture state definition that is based on second posture data from the first posture sensor after reorienting the first posture sensor.

13. The system of claim 8, wherein the processor reorients the first posture sensor by at least reorienting the first posture sensor for a plurality of posture states based on the posture data from the second posture sensor.

14. The system of claim 8, wherein the first posture sensor is arranged proximate a subcutaneous therapy delivery site within the patient, and the second posture sensor is arranged on or within an implantable medical device comprising the processor.

15. The system of claim 8, wherein the processor reorients the first posture sensor by at least:
    determining a first sense posture vector based on the posture data received from the second posture sensor;
    comparing the first sense posture vector to a posture region associated with the second posture sensor to determine a first posture state of the patient, wherein the posture region is defined by posture reference data comprising a first reference coordinate vector;
    subtracting the first reference coordinate vector from the first sense posture vector to determine a difference vector;
    determining a second sense posture vector based on posture data received from the first posture sensor while the patient occupies the first posture state;
    adding the difference vector to the second sense posture vector to determine a second reference coordinate vector for the first posture sensor; and
    defining a reoriented posture region for the first posture sensor corresponding to the first posture state of the patient with posture reference data based at least in part on the second reference coordinate vector.

16. A computer readable medium comprising instructions configured to cause one or more processors to perform a method comprising:
    detecting a change in orientation of a first posture sensor of a therapy system, wherein the therapy system provides posture responsive therapy to a patient; and
    automatically reorienting the first posture sensor based on posture data from a second posture sensor.

17. The computer readable medium of claim 16, wherein the instructions cause the one or more processors to reorient the first posture sensor by at least:
    receiving posture data from the first posture sensor;
    associating the posture data from the first posture sensor with a posture state determined based on the posture data from the second posture sensor; and
    defining a reoriented posture region corresponding to the posture state with posture reference data based at least in part on the posture data from the first posture sensor.

18. The computer readable medium of claim 17, wherein the instructions cause the one or more processors to determine therapy information associated with a first posture state definition that is based on first posture data from the first posture sensor before reorienting the first posture sensor, and associate the therapy information with a second posture state definition that is based on second posture data from the first posture sensor after reorienting the first posture sensor.

19. The computer readable medium of claim 16, wherein the instructions cause the one or more processors to reorient the first posture sensor by at least:
    determining a first sense posture vector based on posture data received from the second posture sensor;
    comparing the first sense posture vector to a posture region associated with the second posture sensor to determine a posture state of the patient, wherein the posture region is defined by posture reference data comprising a first reference coordinate vector;
    subtracting the first reference coordinate vector from the first sense posture vector to determine a difference vector;
    determining a second sense posture vector based on posture data received from the first posture sensor while the patient occupies the posture state;

adding the difference vector to the second sense posture vector to determine a second reference coordinate vector for the first posture sensor; and defining a reoriented posture region for the first posture sensor corresponding to the posture state of the patient with posture reference data based at least in part on the second reference coordinate vector.

20. A system comprising:

means for detecting a change in orientation of a first posture sensor of a therapy system, wherein the therapy system provides posture responsive therapy to a patient; and means for automatically reorienting the first posture sensor based on posture data from a second posture sensor of the therapy system.

21. The system of claim 20, wherein the means for automatically reorienting the first posture sensor based on posture data from a second posture sensor of the therapy system receives posture data from the first posture sensor, associates the posture data from the first posture sensor with a posture state determined based on the posture data from the second posture sensor, and defines a reoriented posture region corresponding to the posture state with posture reference data based at least in part on the first posture sensor posture data.

22. The system of claim 20, wherein the means for automatically reorienting the first posture sensor based on posture data from a second posture sensor of the therapy system determines a first sense posture vector based on posture data received from the second posture sensor, compares the first sense posture vector to a posture region associated with the second posture sensor, wherein the posture region is defined by posture reference data comprising a first reference coordinate vector to determine a posture state of the patient, subtracts the first reference coordinate vector from the first sense posture vector to determine a difference vector, determines a second sense posture vector based on posture data received from the first posture sensor while the patient occupies the posture state, adds the difference vector to the second sense posture vector to determine a second reference coordinate vector for the first posture sensor, and defines a reoriented posture region for the first posture sensor corresponding to the posture state of the patient with posture reference data based at least in part on the second reference coordinate vector.

* * * * *